(12) United States Patent
Babkes et al.

(10) Patent No.: US 9,095,405 B2
(45) Date of Patent: Aug. 4, 2015

(54) SPACE-FILLING INTRAGASTRIC IMPLANTS WITH FLUID FLOW

(75) Inventors: Mitchell H. Babkes, Santa Clarita, CA (US); Zachary Dominguez, Santa Barbara, CA (US); Justin Schwab, Santa Barbara, CA (US)

(73) Assignee: APOLLO ENDOSURGERY, INC., Austin, TX (US)

( * ) Notice: Subject to any disclaimer, the term of this patent is extended or adjusted under 35 U.S.C. 154(b) by 881 days.

(21) Appl. No.: 13/275,211

(22) Filed: Oct. 17, 2011

(65) Prior Publication Data

US 2012/0095495 A1    Apr. 19, 2012

Related U.S. Application Data

(60) Provisional application No. 61/485,009, filed on May 11, 2011, provisional application No. 61/394,592, filed on Oct. 19, 2010.

(51) Int. Cl.
*A61F 5/00* (2006.01)

(52) U.S. Cl.
CPC ............. *A61F 5/0033* (2013.01); *A61F 5/0036* (2013.01); *A61F 5/0086* (2013.01); *A61F 5/0079* (2013.01)

(58) Field of Classification Search
CPC ...... A61F 5/003; A61F 5/0033; A61F 5/0036
USPC ............... 604/96.01, 101.01, 101.03, 101.05, 604/103.07, 103.08; 606/192, 195
See application file for complete search history.

(56) References Cited

U.S. PATENT DOCUMENTS

| 4,416,267 A | 11/1983 | Garren et al. |
| 4,607,618 A | 8/1986 | Angelchik |
| 4,648,383 A | 3/1987 | Angelchik |
| 4,739,758 A | 4/1988 | Lai et al. |
| 4,774,956 A | 10/1988 | Kruse et al. |
| 4,844,068 A | 7/1989 | Arata et al. |
| 4,899,747 A | 2/1990 | Garren et al. |
| 4,925,446 A | 5/1990 | Garay et al. |
| 5,259,399 A | 11/1993 | Brown |
| 5,312,343 A | 5/1994 | Krog et al. |

(Continued)

FOREIGN PATENT DOCUMENTS

| DE | 102007025312 | 11/2008 |
| EP | 1397998 | 3/2004 |

(Continued)

*Primary Examiner* — Thomas McEvoy
(74) *Attorney, Agent, or Firm* — Gordon & Jacobson, PC

(57) ABSTRACT

A variety of passive intragastric implant devices for obesity treatment are disclosed. Such passive devices do not autonomously change shape, but instead react within the stomach to induce satiety. The devices may take up volume within the stomach, thus reducing the intake capacity. Additionally, the devices may contact areas within the stomach, such as the cardia surrounding the esophageal sphincter, to stimulate satiety-inducing nerves. Also, certain devices slow gastric emptying by blocking or otherwise impeding flow through the pyloric sphincter. A number of devices combine two or more of these satiety-inducing features. Methods of implant are disclosed including compressing the devices within a delivery tube and transorally advancing the devices through the esophagus to be deployed within the stomach. Removal of the devices occurs in the reverse.

24 Claims, 13 Drawing Sheets

(56) References Cited

U.S. PATENT DOCUMENTS

| | | | |
|---|---|---|---|
| 5,820,584 A | 10/1998 | Crabb | |
| 6,264,700 B1 | 7/2001 | Kilcoyne et al. | |
| 6,322,538 B1 | 11/2001 | Elbert et al. | |
| 6,454,785 B2 | 9/2002 | De Hoyos Garza | |
| 6,540,789 B1 | 4/2003 | Silverman et al. | |
| 6,579,301 B1 | 6/2003 | Bales et al. | |
| 6,675,809 B2 | 1/2004 | Stack et al. | |
| 6,733,512 B2 | 5/2004 | McGhan | |
| 6,845,776 B2 | 1/2005 | Stack et al. | |
| 6,981,978 B2 | 1/2006 | Gannoe | |
| 6,981,980 B2 | 1/2006 | Sampson et al. | |
| 6,994,095 B2 | 2/2006 | Burnett | |
| 7,008,419 B2 | 3/2006 | Shadduck | |
| 7,033,384 B2 | 4/2006 | Gannoe et al. | |
| 7,037,344 B2 | 5/2006 | Kagan et al. | |
| 7,056,305 B2 | 6/2006 | Garza Alvarez | |
| 7,090,699 B2 | 8/2006 | Geitz | |
| 7,214,233 B2 | 5/2007 | Gannoe et al. | |
| 7,220,237 B2 | 5/2007 | Gannoe et al. | |
| 7,220,284 B2 | 5/2007 | Kagan et al. | |
| 7,223,277 B2 | 5/2007 | DeLegge | |
| 7,320,696 B2 | 1/2008 | Gazi et al. | |
| 7,347,875 B2 | 3/2008 | Levine et al. | |
| 7,354,454 B2 | 4/2008 | Stack et al. | |
| 7,476,256 B2 | 1/2009 | Meade et al. | |
| 7,510,559 B2 | 3/2009 | Deem et al. | |
| 7,608,114 B2 | 10/2009 | Levine et al. | |
| 7,682,330 B2 | 3/2010 | Meade et al. | |
| 7,695,446 B2 | 4/2010 | Levine et al. | |
| 7,699,863 B2 | 4/2010 | Marco et al. | |
| 7,753,870 B2 | 7/2010 | Demarais et al. | |
| 7,771,382 B2 | 8/2010 | Levine et al. | |
| 7,794,447 B2 | 9/2010 | Dann et al. | |
| 7,815,589 B2 | 10/2010 | Meade et al. | |
| 7,837,643 B2 | 11/2010 | Levine et al. | |
| 7,841,503 B2 | 11/2010 | Sonnenschein et al. | |
| 7,931,693 B2 | 4/2011 | Binmoeller | |
| 7,981,162 B2 | 7/2011 | Stack et al. | |
| 8,029,455 B2 | 10/2011 | Stack et al. | |
| 8,032,223 B2 | 10/2011 | Imran | |
| 2003/0109935 A1 | 6/2003 | Geitz | |
| 2003/0153905 A1 | 8/2003 | Edwards et al. | |
| 2004/0044357 A1 | 3/2004 | Gannoe et al. | |
| 2004/0092892 A1 | 5/2004 | Kagan et al. | |
| 2004/0117031 A1 | 6/2004 | Stack et al. | |
| 2004/0122452 A1 | 6/2004 | Deem et al. | |
| 2004/0122453 A1 | 6/2004 | Deem et al. | |
| 2005/0049718 A1 | 3/2005 | Dann et al. | |
| 2005/0055039 A1 | 3/2005 | Burnett et al. | |
| 2005/0085923 A1 | 4/2005 | Levine et al. | |
| 2005/0096692 A1 | 5/2005 | Linder et al. | |
| 2005/0192614 A1 | 9/2005 | Binmoeller | |
| 2005/0197714 A1 | 9/2005 | Sayet | |
| 2005/0267595 A1 | 12/2005 | Chen et al. | |
| 2005/0267596 A1 | 12/2005 | Chen et al. | |
| 2005/0273060 A1 | 12/2005 | Levy et al. | |
| 2006/0178691 A1 | 8/2006 | Binmoeller | |
| 2006/0252983 A1 | 11/2006 | Lembo et al. | |
| 2007/0010864 A1 | 1/2007 | Dann et al. | |
| 2007/0016262 A1 | 1/2007 | Gross et al. | |
| 2007/0021761 A1 | 1/2007 | Phillips | |
| 2007/0078476 A1 | 4/2007 | Hull, Sr. et al. | |
| 2007/0083224 A1 | 4/2007 | Hively | |
| 2007/0100368 A1 | 5/2007 | Quijano et al. | |
| 2007/0118168 A1 | 5/2007 | Lointier et al. | |
| 2007/0149994 A1* | 6/2007 | Sosnowski et al. | 606/192 |
| 2007/0156013 A1 | 7/2007 | Birk | |
| 2007/0173881 A1 | 7/2007 | Birk et al. | |
| 2007/0185374 A1 | 8/2007 | Kick et al. | |
| 2007/0239284 A1 | 10/2007 | Skerven et al. | |
| 2007/0265598 A1 | 11/2007 | Karasik | |
| 2007/0293716 A1 | 12/2007 | Baker et al. | |
| 2008/0015618 A1 | 1/2008 | Sonnenschein et al. | |
| 2008/0058840 A1 | 3/2008 | Albrecht et al. | |
| 2008/0058887 A1 | 3/2008 | Griffin et al. | |
| 2008/0097513 A1 | 4/2008 | Kaji et al. | |
| 2008/0208241 A1 | 8/2008 | Weiner et al. | |
| 2008/0221595 A1 | 9/2008 | Surti | |
| 2008/0234718 A1 | 9/2008 | Paganon et al. | |
| 2008/0234834 A1 | 9/2008 | Meade et al. | |
| 2008/0243166 A1 | 10/2008 | Paganon et al. | |
| 2008/0249635 A1 | 10/2008 | Weitzner et al. | |
| 2008/0255678 A1 | 10/2008 | Cully et al. | |
| 2008/0262529 A1 | 10/2008 | Jacques | |
| 2009/0012553 A1 | 1/2009 | Swain et al. | |
| 2009/0082644 A1 | 3/2009 | Li | |
| 2009/0093767 A1 | 4/2009 | Kelleher | |
| 2009/0149879 A1 | 6/2009 | Dillon | |
| 2009/0198210 A1 | 8/2009 | Burnett et al. | |
| 2009/0259246 A1 | 10/2009 | Eskaros et al. | |
| 2009/0275973 A1 | 11/2009 | Chen et al. | |
| 2009/0287231 A1 | 11/2009 | Brooks et al. | |
| 2009/0299486 A1 | 12/2009 | Shohat et al. | |
| 2009/0312597 A1 | 12/2009 | Bar et al. | |
| 2010/0030017 A1 | 2/2010 | Baker et al. | |
| 2010/0049224 A1 | 2/2010 | Vargas | |
| 2010/0100115 A1 | 4/2010 | Soetermans et al. | |
| 2010/0121371 A1 | 5/2010 | Brooks et al. | |
| 2010/0168782 A1 | 7/2010 | Hancock | |
| 2010/0249822 A1 | 9/2010 | Nihalani | |
| 2010/0256775 A1 | 10/2010 | Belhe et al. | |
| 2010/0256776 A1 | 10/2010 | Levine et al. | |
| 2010/0305590 A1 | 12/2010 | Holmes et al. | |
| 2010/0331756 A1 | 12/2010 | Meade et al. | |

FOREIGN PATENT DOCUMENTS

| | | |
|---|---|---|
| EP | 1774929 | 4/2007 |
| FR | 2892297 | 4/2007 |
| FR | 2941617 | 8/2010 |
| WO | WO 8800027 | 1/1988 |
| WO | 0032092 | 6/2000 |
| WO | 2005094257 | 10/2005 |
| WO | WO 2005/097012 | 10/2005 |
| WO | WO 2005/110280 | 11/2005 |
| WO | 2006044640 | 4/2006 |
| WO | WO 2006/111961 | 10/2006 |
| WO | WO 2006/118744 | 11/2006 |
| WO | WO 2007/027812 | 3/2007 |
| WO | WO 2007053556 | 5/2007 |
| WO | 2007076021 | 7/2007 |
| WO | WO 2007/092390 | 8/2007 |
| WO | WO 2007/110866 | 10/2007 |
| WO | 2008101048 | 8/2008 |
| WO | WO 2008/112894 | 9/2008 |
| WO | WO 2008/132745 | 11/2008 |
| WO | WO 2010/042062 | 4/2010 |
| WO | WO 2010/074712 | 7/2010 |
| WO | WO 2010/087757 | 8/2010 |
| WO | WO 2010/117641 | 10/2010 |

* cited by examiner

9,095,405 B2

SPACE-FILLING INTRAGASTRIC IMPLANTS WITH FLUID FLOW

RELATED APPLICATIONS

The present application claims priority under 35 U.S.C. §119 to U.S. Provisional Application Nos. 61/485,009, filed May 11, 2011, and to 61/394,592, filed Oct. 19, 2010, the disclosures of which are incorporated by reference herein.

FIELD OF THE INVENTION

The present invention is directed to intragastric implants used for the treatment of obesity, and in particular to implants and systems for placement in the stomach cavity that take up space and provide alternative flow paths.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States was estimated to be about 400,000 in 2010.

Examples of surgical methods and devices used to treat obesity include the LAP-BAND® (Allergan Medical of Irvine, Calif.) gastric band and the LAP-BAND AP® (Allergan). However, surgery might not be an option for every obese individual; for certain patients, non-surgical therapies or minimal-surgery options are more effective or appropriate.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These devices are designed to provide therapy for moderately obese individuals who need to shed pounds in preparation for surgery, or as part of a dietary or behavioral modification program. These balloons are typically cylindrical or pear-shaped, generally range in size from 200-500 ml or more, are made of an elastomer such as silicone, polyurethane, or latex, and are filled with air, an inert gas, water, or saline.

One such inflatable intragastric balloon is described in U.S. Pat. No. 5,084,061 and is commercially available as the BioEnterics Intragastric Balloon System ("BIB System," sold under the trademark ORBERA). The BIB System comprises a silicone elastomer intragastric balloon that is inserted into the stomach and filled with fluid. Conventionally, the balloons are placed in the stomach in an empty or deflated state and thereafter filled (fully or partially) with a suitable fluid. The balloon occupies space in the stomach, thereby leaving less room available for food and creating a feeling of satiety for the patient. Placement of the intragastric balloon is non-surgical, trans-oral, usually requiring no more than 20-30 minutes. The procedure is performed gastroscopically in an outpatient setting, typically using local anesthesia and sedation. Placement of such balloons is temporary, and such balloons are typically removed after about six months. Removing the balloon requires deflation by puncturing with a gastroscopic instrument, and either aspirating the contents of the balloon and removing it, or allowing the fluid to pass into the patient's stomach. Clinical results with these devices show that for many obese patients, the intragastric balloons significantly help to control appetite and accomplish weight loss.

Some attempted solutions for weight loss by placing devices in the stomach result in unintended consequences. For instance, some devices tend to cause food and liquid to back up in the stomach, leading to symptoms of gastroesophageal reflux disease (GERD), a condition in which the stomach contents (food or liquid) leak backwards from the stomach into the esophagus. Also, the stomach acclimates to some gastric implant devices, leading to an expansion of stomach volume and consequent reduction in the efficacy of the device.

Therefore, despite many advances in the design of intragastric obesity treatment implants, there remains a need for improved implants that can be implanted for longer periods than before or otherwise address certain drawbacks of intragastric balloons and other such implants.

SUMMARY OF THE INVENTION

The present invention addresses the above-described problems by providing passive intragastric apparatuses and methods for inducing satiety and therefore treating obesity. Such passive devices do not autonomously change shape, but instead react within the stomach to induce satiety. The devices may take up volume within the stomach, thus reducing the intake capacity. Additionally, the devices may contact areas within the stomach, such as the cardia surrounding the esophageal sphincter, to stimulate satiety-inducing nerves. Also, certain devices slow gastric emptying by blocking or otherwise impeding flow through the pyloric sphincter. A number of devices combine two or more of these satiety-inducing features. Methods of implant are disclosed including compressing the devices within a delivery tube and transorally advancing the devices through the esophagus to be deployed within the stomach. Removal of the devices occurs in the reverse.

One embodiment of a passive intragastric obesity treatment implant disclosed herein comprises an inflatable body having a length sufficient to extend between the esophageal sphincter and the pyloric sphincter upon implant in the stomach, and a width sufficient to contact the interior stomach walls upon contraction thereof. The body is rounded and slightly tapered so as to generally conform to the volume of an adult stomach cavity. The body further includes a plurality of or a series of chambers fluidly connected so as to be capable of simultaneous inflation and deflation. Two chambers at a proximal end are separated by an annular recess that is positioned to open to the esophageal sphincter, wherein apertures in the annular recess open to a central flow channel that extends from the annular recess to an inferior end of the body, and some of the chambers surround the central flow channel. The implant is formed of a material which permits it to be compressed into a substantially linear delivery configuration and that will resist degradation over a period of at least six months within the stomach. The central flow channel desirably has a star-shaped cross-section. The implant further may include a plurality of circumferential grooves extending around the body and between adjacent chambers, and radial passages connecting the circumferential grooves to the central flow channel. The chambers preferably gradually decrease in diameter from the superior to the inferior ends of the body. The body may have a rounded superior end that mimics the shape of the surrounding cardia and defines a proximal chamber therein.

Another passive intragastric obesity treatment implant comprises a foam body having a sufficient diameter so as to contact the interior stomach walls upon contraction thereof, the foam body defining a central throughbore. A radially expandable and compressible stent lines the central throughbore, the stent having a tubular wall and struts across a proximal end to filter larger food particles. The implant is formed of a material which permits it to be compressed into a substantially linear delivery configuration and that will resist degradation over a period of at least six months within the stomach. The struts at the proximal end of the stent may be formed in a web of angled struts that extend inward from the tubular wall and are joined together by a ring. The foam body preferably has a diameter of between about 10-20 cm.

A still further embodiment comprises a collapsible body defining a large bowl-shaped proximal end having a diameter sufficient to contact the interior stomach walls upon contraction thereof. The proximal end has an artificial stoma opening through a bottom of the bowl shape. The body further includes a tapered hollow leg extending distally from the proximal end and an enlarged pyloric member on the distal end of the leg. The implant is formed of a material which permits it to be compressed into a substantially linear delivery configuration and that will resist degradation over a period of at least six months within the stomach. In a preferred embodiment, the body has an ear-horn shape narrowing from the bowl-shaped proximal end along the leg to the pyloric member. The leg includes a plurality of large apertures to permit ingress of stomach juices to the interior of the leg. The body may be inflatable, and the stoma opening communicates with a flow-through passage that extends to the outside of the leg.

In a still further embodiment of a passive intragastric obesity treatment implant, a hollow flexible tether has a lumen and a length sufficient to extend substantially the entire length of the stomach cavity from the pyloris to the esophageal/stomach junction and for a distance into the esophagus. A detention tray affixes to a proximal section of the tether and has a size that impedes free passage of food boluses entering the stomach from the esophagus. A series of inflatable balloons are affixed to the tether and are in fluid communication with the lumen so as to be able to receive fluid from and be filled by fluid in the tether. The inflatable balloons include a pyloric balloon at a distal end of the tether having a size that will not pass through the pyloric sphincter. Further, the detention tray is positioned on the tether relative to the pyloric balloon so as to be located adjacent the cardia. The implant is made of a material that will resist degradation over a period of at least six months within the stomach. The detention tray is preferably non-inflatable.

In one form, the detention tray is bowl-shaped with a concave proximal side. One of the inflatable balloons may be a positioning balloon sized larger than the others and positioned on the tether just distal to the detention tray so that it contacts the surrounding cardia and centers the tether and tray below the esophageal/stomach junction. The positioning balloon may have an arcuate outer section connected by spokes to a middle portion through which the tether passes, and the outer section may define a full circle. The pyloric balloon is desirably shaped like a donut with a central through hole that permits passage of chyme from the stomach to the pyloric sphincter. The inflatable balloons further may include the pyloric balloon and a pair of spherical intermediate balloons between the pyloric balloon and the detention tray, the intermediate balloons maintaining a space between the tether and the stomach wall. Finally, the implant may further include a fill valve fitted to a proximal end of the tether, the fill valve having structure for mating with a fill tube nipple.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

The present invention is directed to a variety of different intragastric devices that passively treat obesity by taking up space within the stomach or contact areas in and around the stomach to induce feelings of satiety. Furthermore, some devices described herein affect the rate of stomach emptying. It should be understood that a number of the disclosed devices provide more than one of these passive aspects, and also that any disclosed structure could be combined with another disclosed structure unless physically impossible. As such, combinations of the passive satiety-inducing features disclosed herein, even if not explicitly stated, are contemplated. The term "passive" refers primarily to a lack of any moving parts within the devices, but in general to the inert nature of the various devices. A passive device as defined herein, however, is not one that cannot affect change or stimulate the stomach, but rather one that may do so without any physical or chemical changes to its basic makeup.

Figure 1:
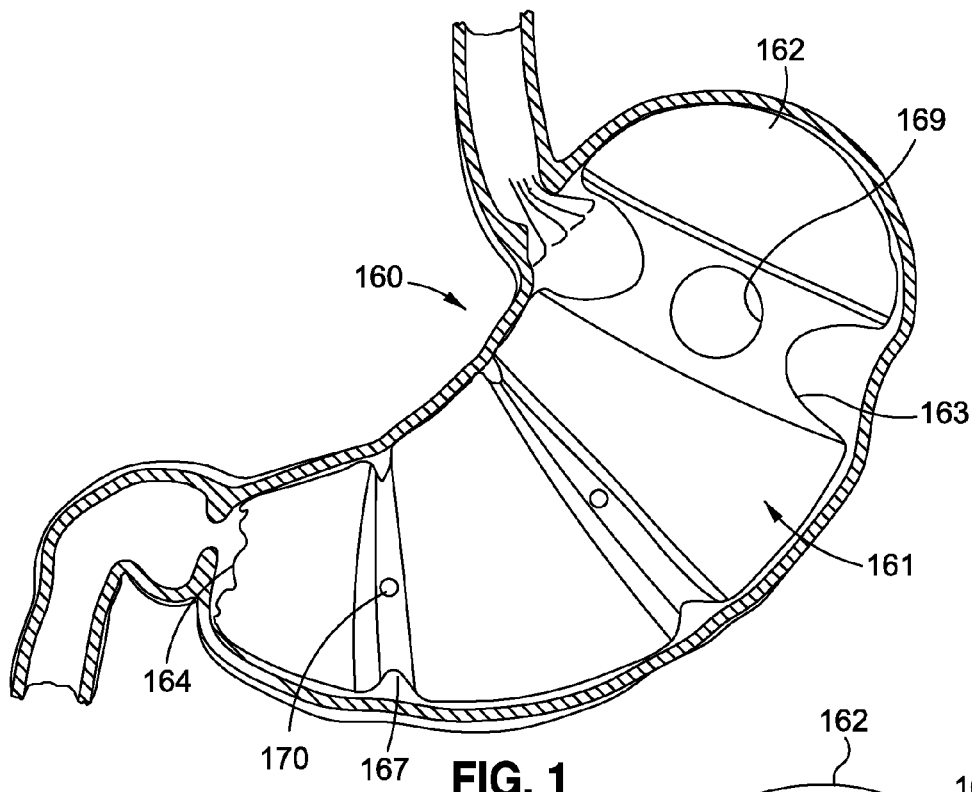
FIG. 1 illustrates an intragastric obesity device that substantially fills the stomach cavity and includes a flow-through channel therein.

FIG. 1 illustrates a first space-occupying device 160, but also illustrates the anatomy of the human stomach, which will be described first. The major function of the stomach is to temporarily store food and release it slowly into the duodenum. The esophagus extending downward from the mouth connects to the stomach via esophageal sphincter, which regulates flow food into the stomach cavity. The cardia surrounds the superior opening of the stomach. The rounded portion superior to the body and adjacent the cardia is the fundus. Inferior to the fundus is the large central portion of the stomach, called the body, that is lined with muscles that contract and relax repetitively to churn the food therein. The stomach processes the food to a semi-solid "chyme," which enables better contact with the mucous membrane of the intestines, thereby facilitating absorption of nutrients. In addition, the stomach is an important site of enzyme production.

Lower down in the stomach the antrum connects the body to the pyloris, which leads into the duodenum. Below the stomach, the duodenum leads into the upper part of the small intestine (not shown); the jejunum makes up about one-third of the small intestine. The region of the stomach that connects to the duodenum is the pylorus. The pylorus communicates with the duodenum of the small intestine via the pyloric sphincter (valve). This valve regulates the passage of chyme from stomach to duodenum and it prevents backflow of chyme from duodenum to stomach.

Figure 2:
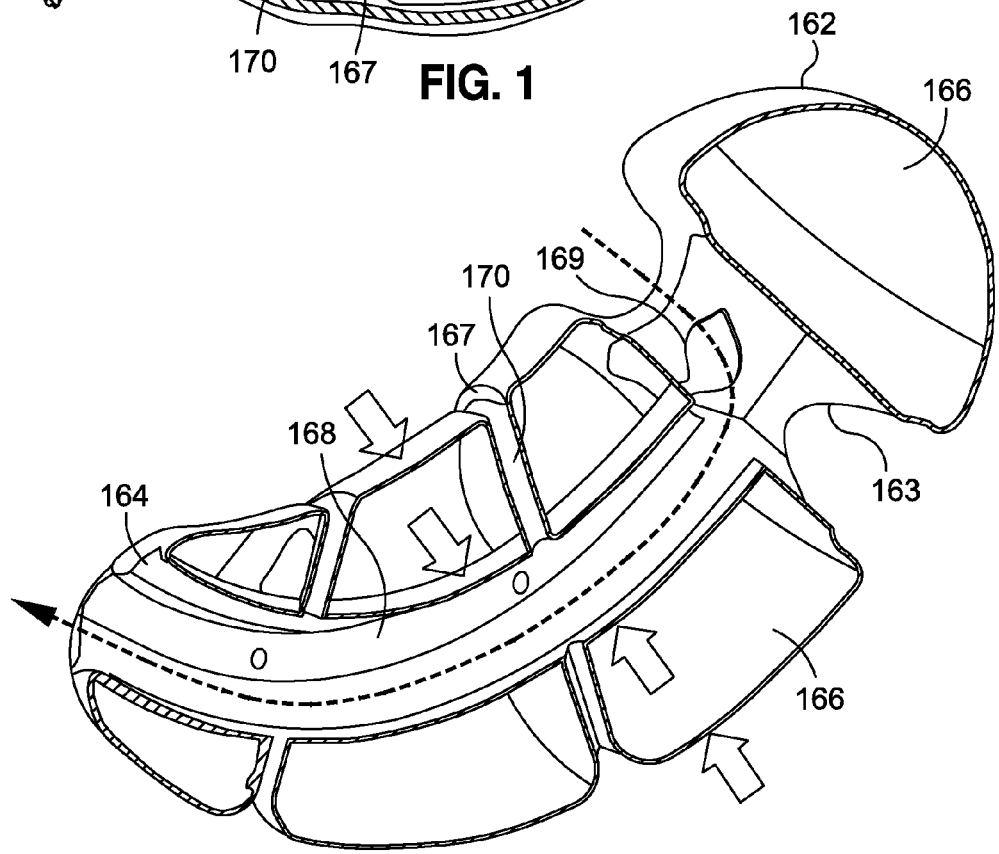
FIG. 2 is a longitudinal sectional view thereof illustrating fluid flow and peristaltic action with arrows.

Certain devices disclosed herein have flow-through channels and entirely or almost-entirely fill the stomach. For instance, a stomach-in-stomach device 160 shown in FIGS. 1-3 includes an inflated soft body 161 that conforms to the stomach and is generally convex. The device 160 has a rounded superior end 162 that abuts the cardia, an annular recess 163 adjacent thereto, and a gradually tapered and curved inferior portion that conforms to the greater curvature of the stomach and terminates in a scalloped inferior end 164. The inflated body 161 seen in longitudinal section within the stomach in FIG. 2 comprises a series of chambers 166 fluidly connected so as to be capable of simultaneous inflation and deflation. Besides a chamber 166 at the superior end 162, the body 161 has three annular chambers 166 delimited by exterior circumferential grooves 167 and surrounding an inner generally longitudinal flow channel 168. The three chambers 166 gradually decrease in diameter from the superior to the inferior end of the device 160. The flow channel 168 extends from the annular recess 163 to the inferior end 164. A series of apertures 169 open the inner channel 168 to the annular recess 163 near the superior end 162. Radial passages 170 extend between the circumferential grooves 167 and the inner flow channel 168.

Figure 3:
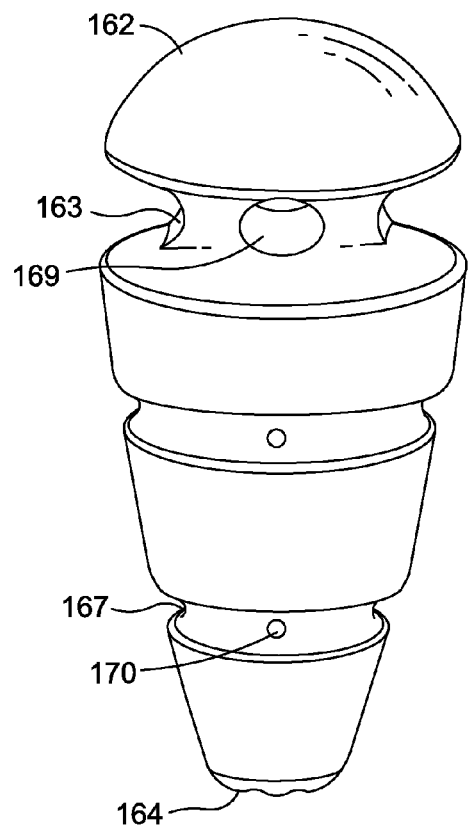
FIG. 3 is a perspective of the device of FIG. 1 prior to implant.

The device 160 is a saline-filled, soft, balloon-like structure shown in a pre-implant state in FIG. 3, which occupies and conforms to the entire stomach cavity. Once implanted and inflated, the device 160 assumes an arcuate path as it conforms to the stomach cavity, as in FIGS. 1 and 2. Due to the device size, available stomach volume is drastically reduced, so volume in which food mass may reside is far less than normal, and a feeling of satiety will occur sooner. As seen by the dashed-line arrow in FIG. 2, solid and liquid matter enters the annular recess 163 from the esophagus and passes inward to the inner channel 168 through the apertures 169. The inner flow channel 168 through the center connects the upper stomach to the lower, without obstruction of the pylorus and subsequent delayed gastric emptying. The flow channel 168 has a star-like cross sectional shape such that peristaltic action of the stomach walls (inward arrows shown in FIG. 2) will transfer through to the "sharp-walled" center channel, via hydraulic compression, and the mechanical action upon the food will be improved as compared to a round channel. The central flow channel 168 acts as a smaller than normal stomach, so food intake cannot be as great as before device placement.

Although the primary food pathway is forced through the central flow channel 168, some leakage around the device 160 will likely occur, which is acceptable. The grooves 167 in the outside walls of the device 160 help channel small solids and liquids to the smaller passages 170 that radiate toward the larger, central channel 168. Smaller particles and some liquids may pass directly into the pylorus through the scalloped atrium end 164 of the channel 168.

Additionally, the rounded superior end 162 of the device 160 presses against cardia, thereby triggering release of satiety-inducing hormones, signaling the body to stop eating. The inflated device substantially fills the stomach cavity which maintains contact with the cardia. However, during food intake, the churning of the stomach walls will naturally squeeze the device 160, such that the superior end 162 will pressurize and apply greater force to the cardia.

For device insertion, a lubricated, Teflon or similar material, thin-walled tube would be inserted down the esophagus, and partially into the stomach, with the device compressed and pre-loaded inside the tube. Then the device would be maintained in its location by using a foot-ended wire or similar obturator, to bear on the compressed mass, and the delivery tube would be pulled back up the esophagus, and extracted through the mouth, leaving the device in place. While the tube is removed, the resiliency of the material causes the device to "spring open" to its original/non-compressed shape. A valve (not shown) near the superior end may be provided for saline filling the body 161.

Figure 4:
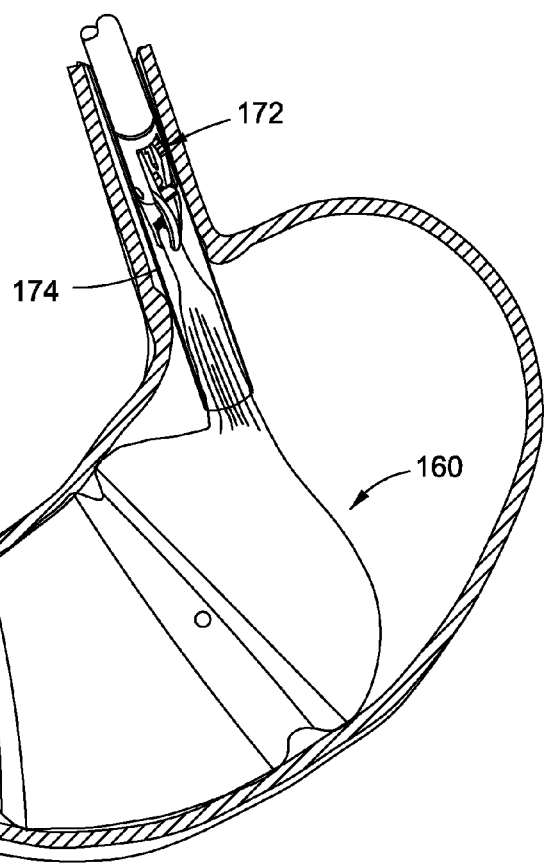
FIG. 4 illustrates the device of FIG. 1 being removed from the stomach cavity.

For device removal, as seen in FIG. 4, a lubricated tube 172 extends down through the esophageal sphincter and into proximity with the superior end 162. A wire or other device is used to deflate the body 161, and the saline simply drains into the stomach. A grabber 174 passed down the removal tube 172 then grabs the superior end of the body 161 and pulls the device 160 into the tube. Because of the extremely soft and flexible material used, such as certain fluoroelastomers, the device 160 collapses easily into the tube 172.

Another device 180 that has a flow-through channel and almost-entirely fills the stomach is shown in FIGS. 5-8. This device 180 occupies volume within the stomach; however, its main mode of action is the ability to exert pressure on the stomach walls in order to induce feelings of fullness.

Figure 5:
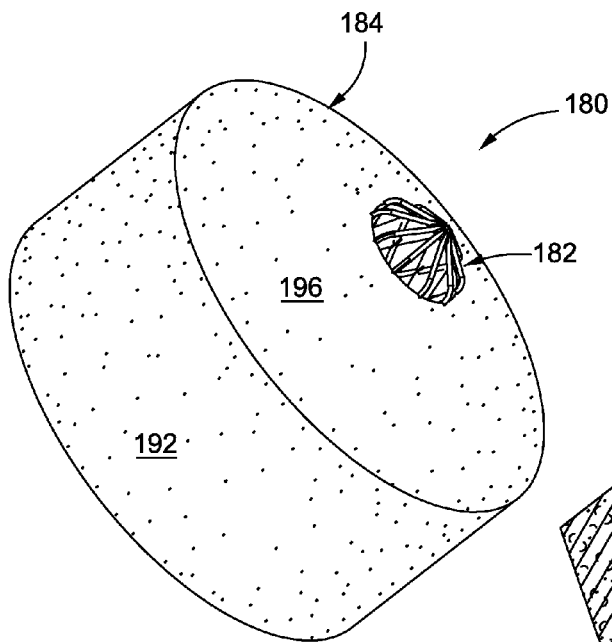
FIG. 5 is a perspective view of an alternative stomach-filling intragastric device having a foam body and a flow-through channel.
Figure 5A:
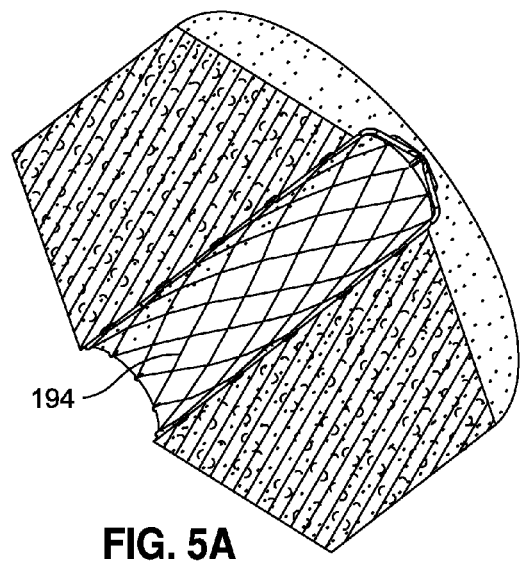
FIG. 5A is a longitudinal sectional view therethrough.

The device 180 consists of a collapsible tubular stent 182 surrounded by a generally annular foam body 184, and is seen pre-implant in FIGS. 5 and 5A. The stent 182 provides a filtered pathway for food in the stomach to pass, which should limit the likelihood of gastroesophageal reflux disease (GERD). While providing some rigid structure to the device 180, the stent 182 is also compliant enough in the radial direction to both facilitate implantation/explantation and accommodate stomach contractions.

Figure 6:
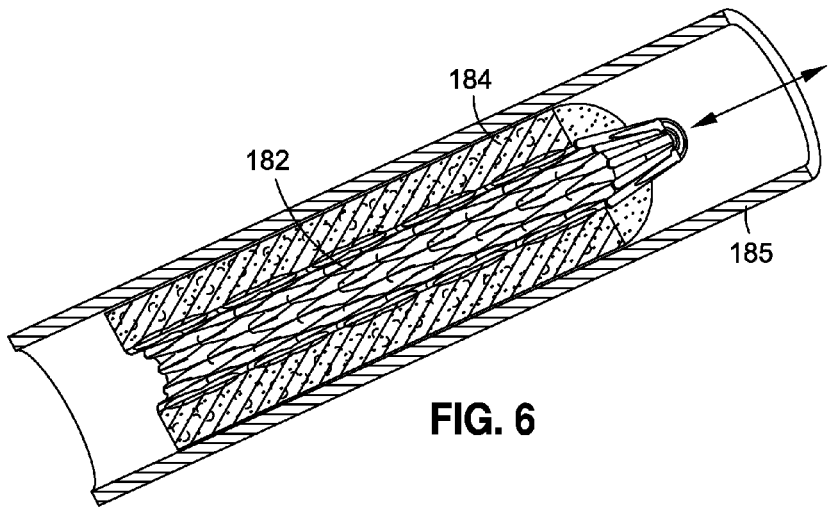
FIG. 6 is a perspective sectional view of the device of FIG. 5 compressed within a delivery tube.
Figure 7A:
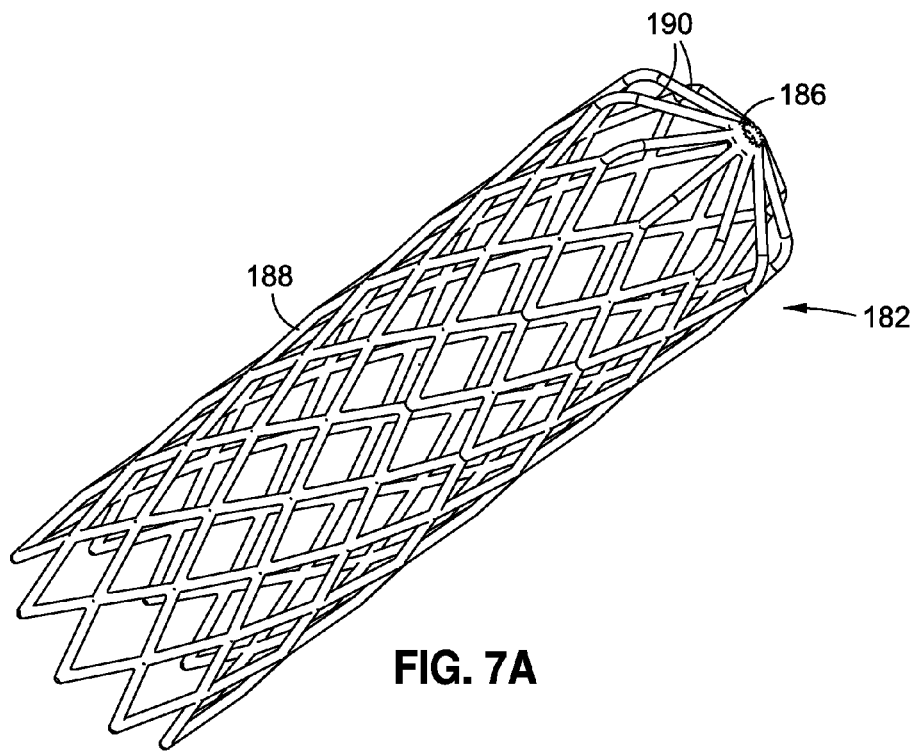
FIGS. 7A and 7B are expanded and contracted perspective views of a stent that lines the flow-through channel of the device of FIG. 5.
Figure 7B:
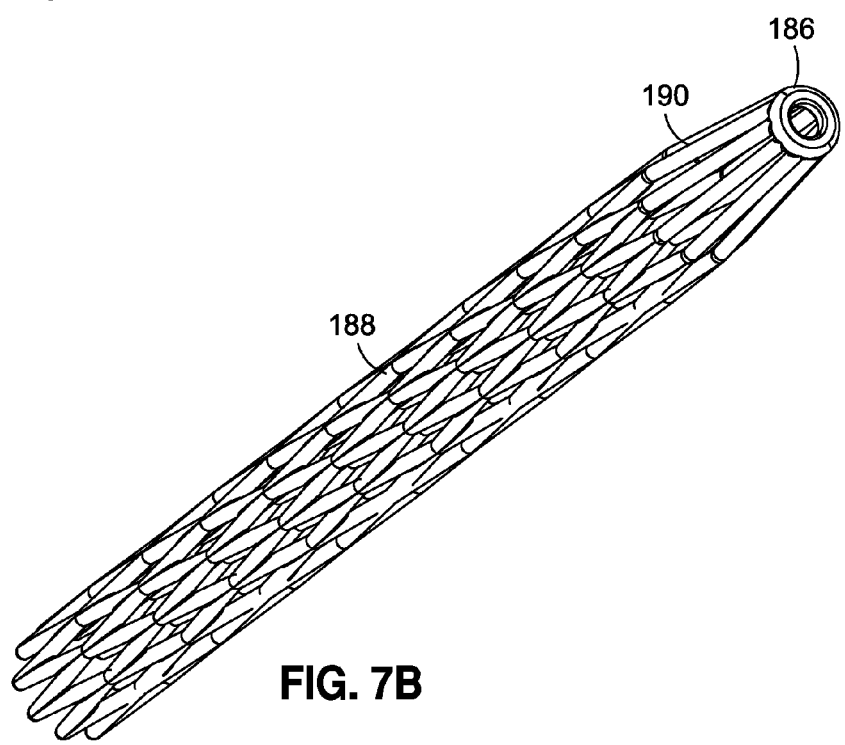

The stent 182 is normally expanded, but can be compressed to a size that allows for insertion and removal through a tube 185 passed through the esophagus, as seen in FIG. 6. A proximal end of the stent 182 is equipped with a ring 186 as seen in FIGS. 7A/7B that allows for either a custom or standard endoscopic tool to pull the stent into a sheath which collapses the structure. The stent 182 has a tubular wall 188 formed of a latticework of interconnected struts that permit radially compression and expansion. A web of angled struts 190 on the proximal end extend inward from the wall 188 and are joined together by the ring 186. The angled struts 190 act as a filter for larger solid particles which helps slow stomach emptying and may encourage a feeling of satiety if the proximal end of the device 180 is positioned close to the cardia. In contrast to some other prior intragastric implants, the continually open passageway through the device 180 helps prevent GERD. The stent 182 may be made from materials including (but not limited to) rubbers, fluorosilicones, fluoroelastomers, thermoplastic elastomers, thermoplastics, thermosets, metals, or any combinations thereof.

Figure 8:
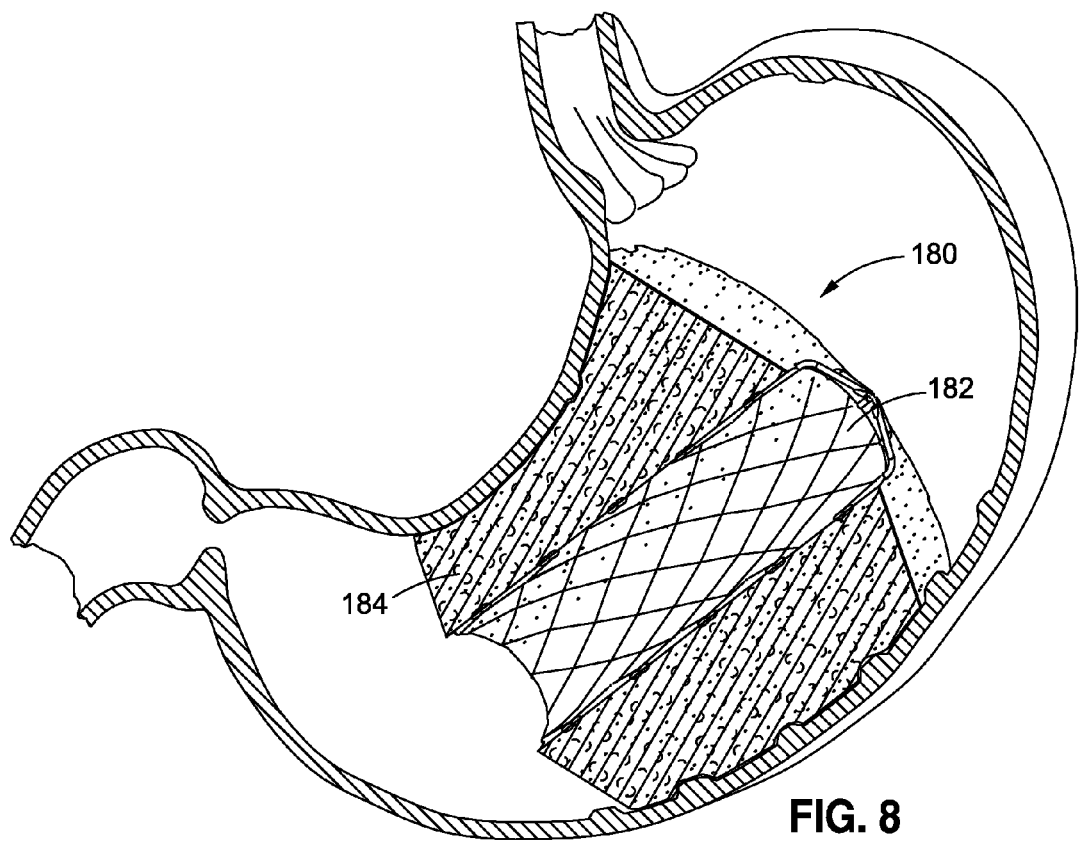
FIG. 8 illustrates the device of FIG. 5 implanted within a stomach cavity.
Figure 8A:
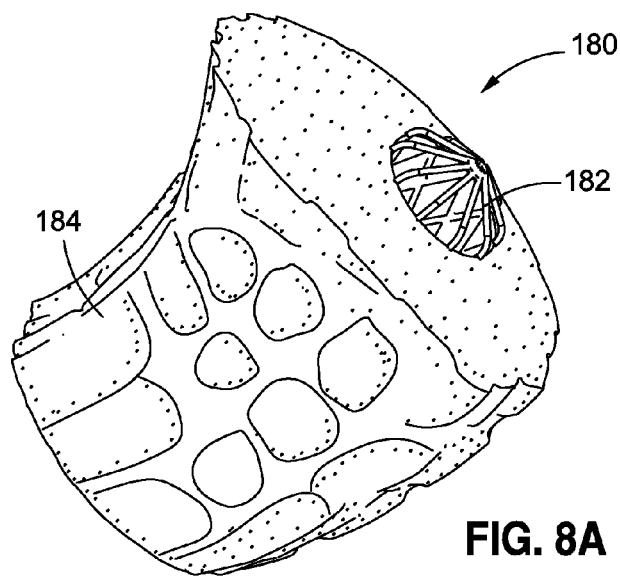
FIG. 8A shows the shape of the device as it looks in the stomach cavity.

The sponge like, foam body 184 (open or closed cell) surrounding the stent 182 fills the space across the stomach cavity, though does not extend the full length of the stomach, as seen in FIG. 8. In a preferred embodiment, the axial dimension of the foam body 184 is between about 10-20 cm. The foam body 184 in its relaxed, uncompressed configuration as seen in FIG. 5 has a cylindrical outer surface 192, a cylindrical inner bore 194 that closely receives the stent 182, and outwardly-projecting conical end surfaces 196. The foam body 184 conforms to the shape of the stomach cavity when implanted, as seen in FIG. 8A. The foam material is durable enough to withstand the gastric environment and may be manufactured from materials including (but not limited to) rubbers, fluorosilicones, fluoroelastomers, thermoplastic elastomers, or any combinations thereof. The foam body 184 acts as a spring within the stomach, continually placing pressure on the gastric walls, independent of changes in the stomach shape and size. Because the stomach is an ever changing organ (in shape and size) both in the long term (remodeling of the stomach after sustained changes in its environment) and short term (stomach contractions, various body positions), it is difficult to create a single device which can maintain pressure on the gastric walls over a long period of time consistently. The diameter of the foam body 184 needs to be sufficiently large such that even in a large stomach, the foam exerts pressure on the gastric walls. In an exemplary embodiment, the diameter of the foam body 184 is between about 10-20 cm.

Figure 9:
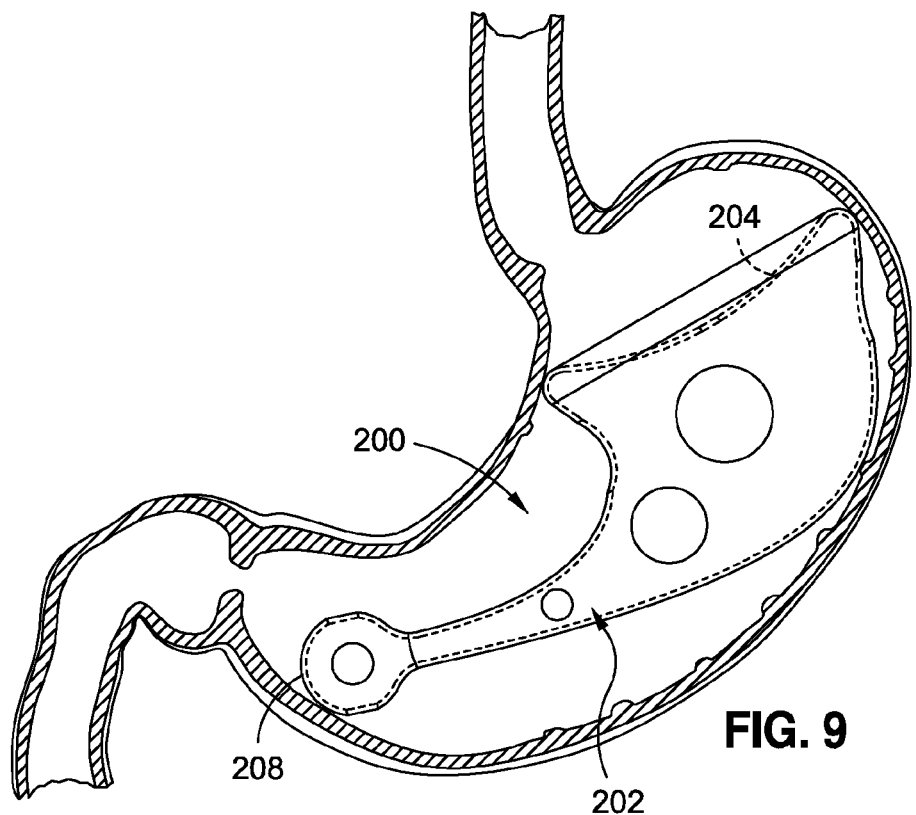
FIG. 9 shows a still further intragastric obesity treatment device within the stomach having an upper bowl-shaped member with an artificial stoma.
Figure 9A:
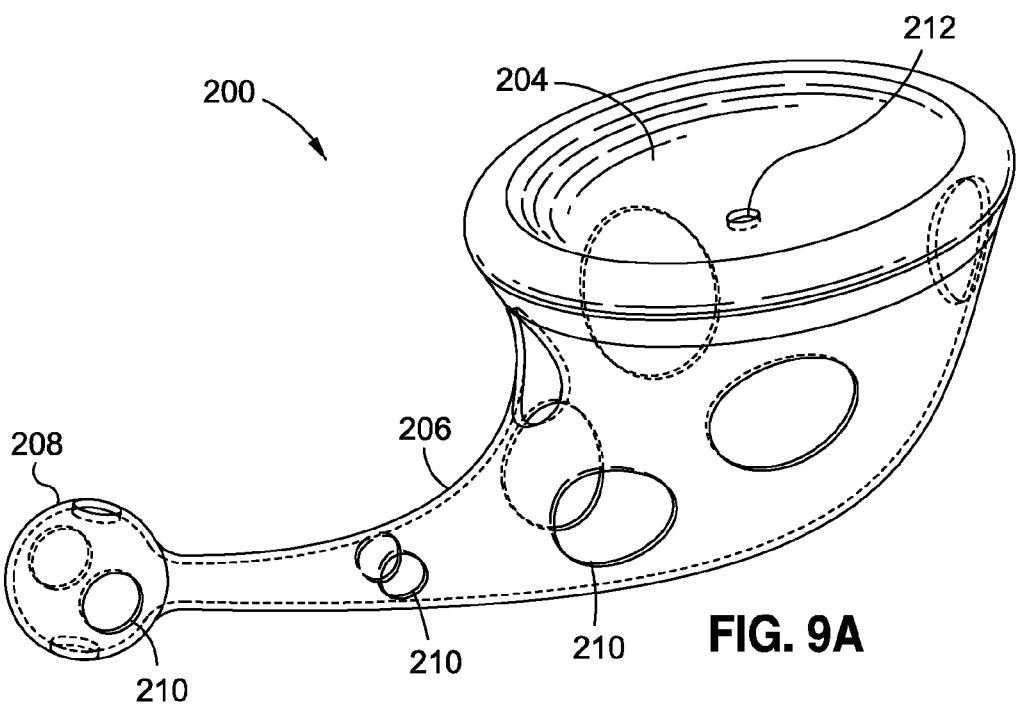
FIG. 9A is a perspective view of the device.

The foam can be compressed and held in place during implantation and explantation as in FIG. 6. Once implanted, the foam body 184 expands to conform to the approximate shape of the stomach. This pressure on the stomach walls encourages a feeling of fullness, without inhibiting normal passage of food through the GI system. The absolute and relative sizes of the foam body 184 outer surface and inner bore diameters may be adjusted for different patients, with the bore diameter affecting the rate of flow of solid and liquid matter therethrough. In one embodiment, the inner bore diameter of the foam body 184 is between about 2-4 cm A still further device 200 that provides a flow-through space is shown in FIGS. 9 and 9A, and comprises an implantable ear-horn-shaped body 202 with a large bowl-shaped proximal end 204 tapering down in a distal direction along a hollow leg 206 to a hollow spherical pyloric member 208. The hollow leg 206 and pyloric member 208 are both interrupted by a plurality of apertures 210 that permit fluid communication between the inside and the outside of the hollow structures. Although hollow, the device 200 is not an inflated balloon. Rather, the material used provides sufficient stiffness to maintain the ear-horn shape as shown.

The device 200 is formed of a flexible material that allows it to be compressed and pre-loading into a delivery tube (not shown) for esophageal insertion into the stomach. Deployment of the device 200 within the stomach cavity permits expansion of the device into the position shown in FIG. 9, with the bowl-shaped proximal end 204 facing the esophagus and the pyloric member 208 located within the pylorus. Device removal is accomplished using a standard grabber down a similar tube which has been inserted down the esophagus, so the entire device can be pulled back into the tube and removed therewith.

The diameter and concavity of the bowl-shaped proximal end 204 allows it to contact the stomach cavity walls and intercept food and liquid entering through the esophageal sphincter. The proximal end 204 acts as a detention tray positioned just inside the stomach from the esophageal sphincter that presents a barrier to incoming food bound for the stomach, but which eventually overflows its contents into the stomach. A small drain hole 212 acts as an artificial stoma and permits a limited amount of food and liquid past the proximal end 204 and into the cavity of the body 202. From there, gastric juices mixed with the food particles and begin the process of breaking them down into chyme. The body 202 is sufficiently flexible so that contractions of the stomach muscles are transmitted therethrough. The diameter of the spherical pyloric member 208 is sufficiently large that it cannot pass through the pyloric sphincter.

Because of the length of the body 202, and the curved shape of the device 200, the proximal end 204 contacts the walls around the esophageal junction, and against the cardia. In addition, the hollow leg 206 serves as an anti-rotational feature to help hold the device in place, and allow it to return to a normal position as shown, after peristaltic waves in the stomach.

Figure 10:
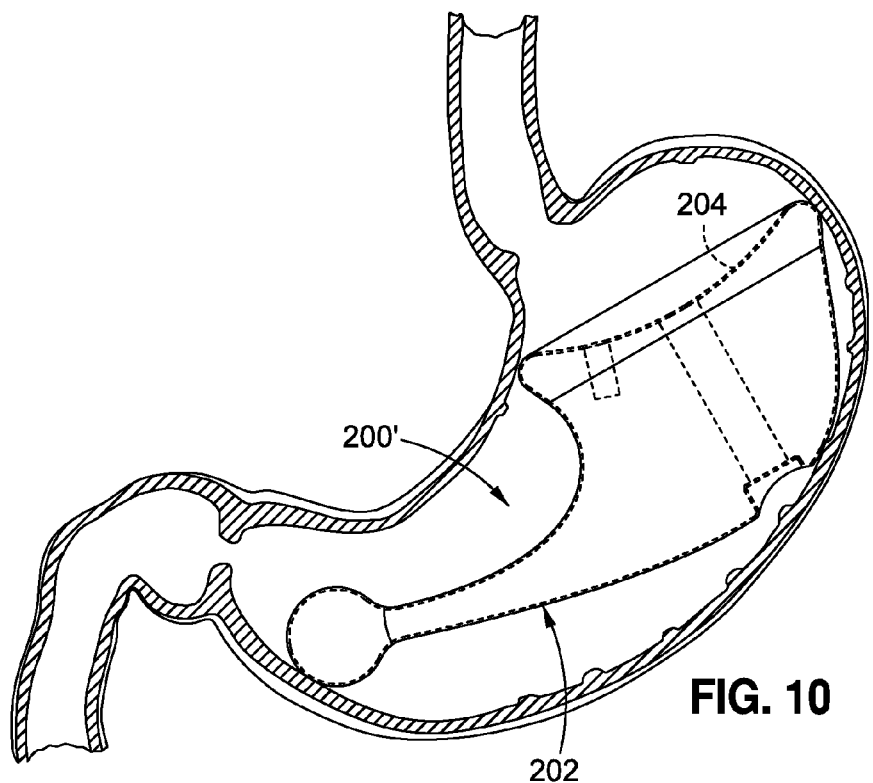
FIG. 10 is an alternative device having an artificial stoma similar to that in FIG. 9 implanted in the stomach.
Figure 10A:
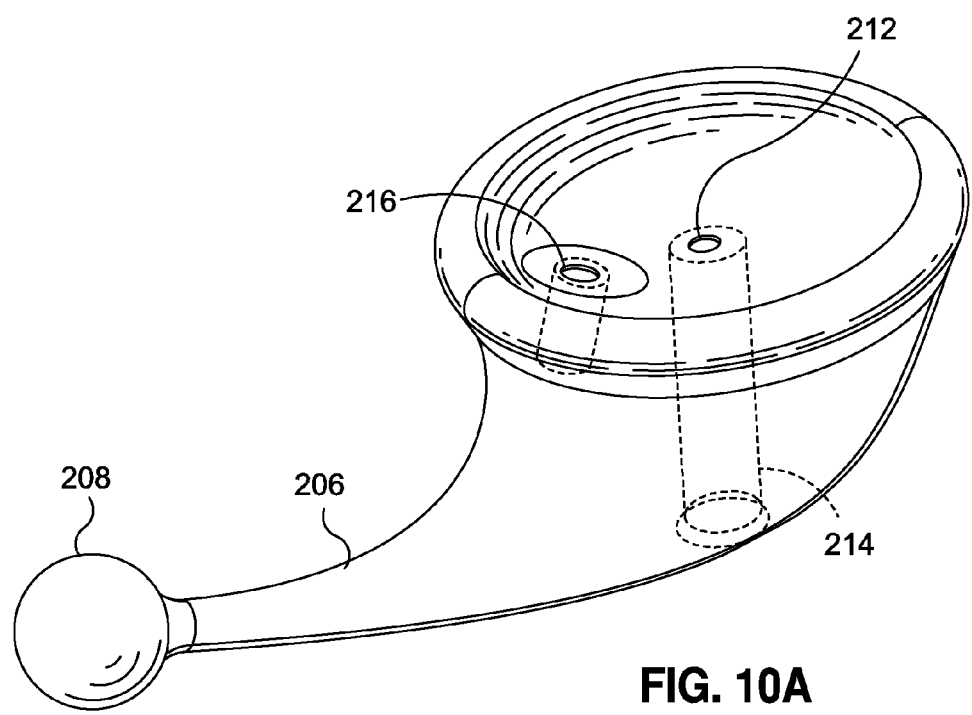
FIG. 10A is a perspective view of the alternative device.

In a second embodiment seen in FIGS. 10 and 10A, an ear-horn-shaped device 200' is configured the same as and works essentially like the device 200 of FIG. 9, except the device is a thinner-walled (hollow) balloon, intended to be saline-filled once inside the stomach. As such, like features will be given the same element numbers.

The second embodiment 200' has a tube 214 that extends between the drain hole 212 and an opposite surface of the body 202, on the convex side thereof. In this embodiment, food that passes through the drain hole 212 does not enter the interior of the inflated body 202, but instead passes to the opposite side. The tube 214 tethers the bowl-shaped proximal end 204 to the opposite surface of the balloon, so when saline-filled, the concave bowl shape is retained. As in the first embodiment, the amount of food caught by and contained in the concave bowl 204 is far less than can be held in an empty stomach. In both embodiments, when food enters the bowl 204 it accumulates and applies pressure to the cardia, thereby stimulating release of satiety-inducing hormones.

Deployment of the device 200' within the stomach cavity is similar to the earlier embodiment, but once deployed in the cavity the user inflates the body 202 through a fill valve 216 provided in the concave proximal end 204. Removal of the inflated device 200' is accomplished by inserting a tube down the esophagus, and clippers down the tube. The device 200' can then be clipped to evacuate the saline, and a standard grabber can then be employed to pull the deflated balloon back into the tube for removal therewith. In the second embodiment, size adjustability is possible by removing or adding saline, whereas the first embodiment may be supplied in a few different sizes.

Some food will normally leak out into the stomach, around the upper rim of the bowl 204, where it contacts the stomach lining. The remaining food passes through the centrally-located small stoma 212, and into the stomach. The inflated embodiment 200' is thought to have a more compliant stoma than the non-inflated version 200, so food passage can be somewhat easier.

FIGS. 11-16 illustrate additional intragastric devices that effect cardial stimulation to signal the brain to release the satiety-inducing hormones, which eventually slows eating, resulting in weight loss. These devices feature a detention tray positioned just inside the stomach from the esophageal sphincter that presents a barrier to incoming food bound for the stomach, but which eventually overflows its contents into the stomach. Much as prior art gastric bands restrict the free flow of boluses of food into the stomach, the detention trays cause a temporary backup of food at the esophageal/stomach junction, which inevitably contacts the surrounding cardial walls and stimulates satiety.

As with earlier devices, those shown in FIGS. 11-16 are intended to be transorally placed, without the need for laparoscopic or other surgical assist, and without the need for piercing of tissues to physically anchor the device. Further, these devices are intended to maintain their position without the need for stent-anchoring within the esophagus. Without some type of permanent positioning method, however, migration of a stomach-implanted device can occur, with limited chance of the device ever returning to its intended position. Instead, these devices achieve their "anchoring" by loosely maintaining their position and "springing back" whenever moved. This is achieved by way of a hollow tether with a springy/stiff consistency and a length spanning the length of the stomach from the pylorus to the cardia, so as to loosely hold the device in position. The springy stiffness is due to either the use of a fairly stiff material for the tether itself, such a polypropylene, or via a co-extruded spring of various materials (e.g., Nitinol), molded within the lumen walls. The advantageous features of these devices will be clear after reading the detailed description below.

Figure 11:
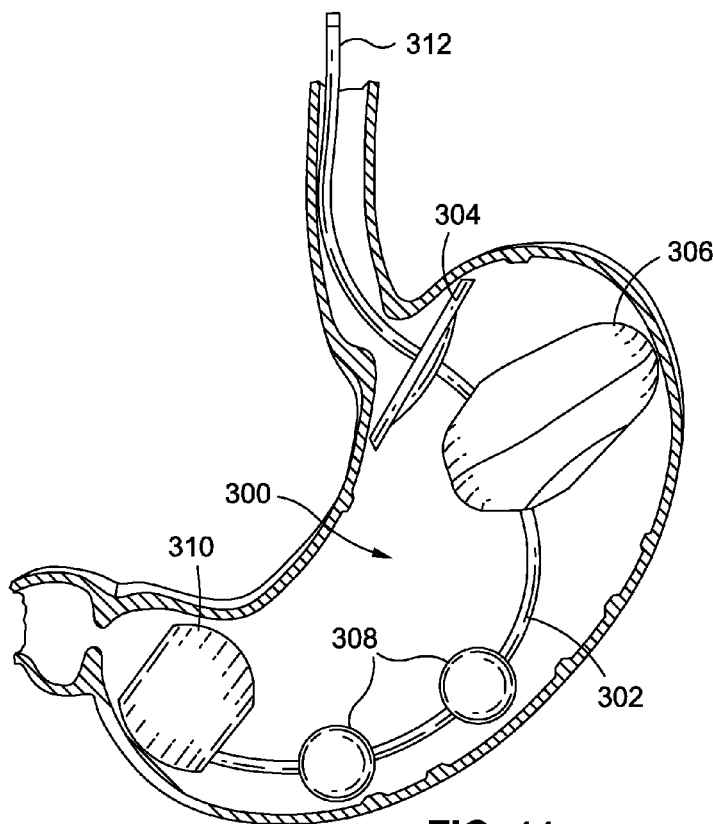
FIG. 11 shows an intragastric device including a series of tethered elements within the stomach cavity that support a detention tray just below the esophageal sphincter.

FIG. 11 shows an intragastric device 300 including a series of elements spaced apart ("daisy-chained") within the stomach cavity and connected by a tether 302 that supports a detention tray 304 just below the esophageal sphincter. The device 300 has a length sufficient to extend substantially the entire length of the stomach cavity from the pyloris to the esophageal/stomach junction and for a distance into the esophagus. The device 300 includes a saline-filled proximal positioning balloon 306, a plurality of intermediate balloons 308, and a pyloric balloon 310, together which support/hold the tether 302 between the lesser and greater curvatures of the stomach. That is, the tether 302 remains spaced from the stomach walls, and is curved to fit the anatomy, generally tracking the greater curvature of the stomach. The balloons 306, 308, 310 can be provided in various configurations, as will be seen with the proximal positioning balloon 306. In addition to helping hold the device 300 in place as stomach movement occurs, the volume of the balloons, and the positioning balloon 306 in particular, are also space-occupying, similar to prior art spherical bioenteric balloons such as the Orbera® System from Allergan Medical of Irvine, Calif. For instance, the aggregate volume of the balloons 306, 308, 310 may occupy approximately the same volume (400 ml) as the aforementioned Orbera® System, which is proven sufficient to facilitate weight loss.

Figure 12C:
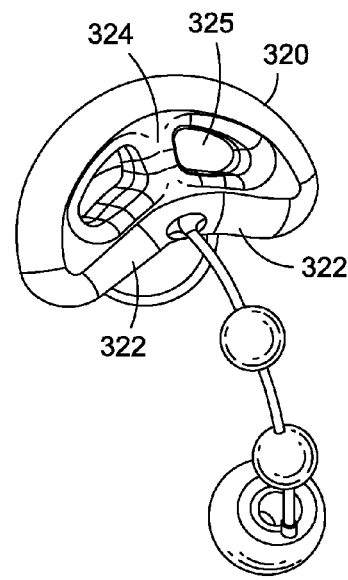
FIGS. 12A-12C are isolated perspective and longitudinal sectional views of the device of FIG. 11.
Figure 12A:
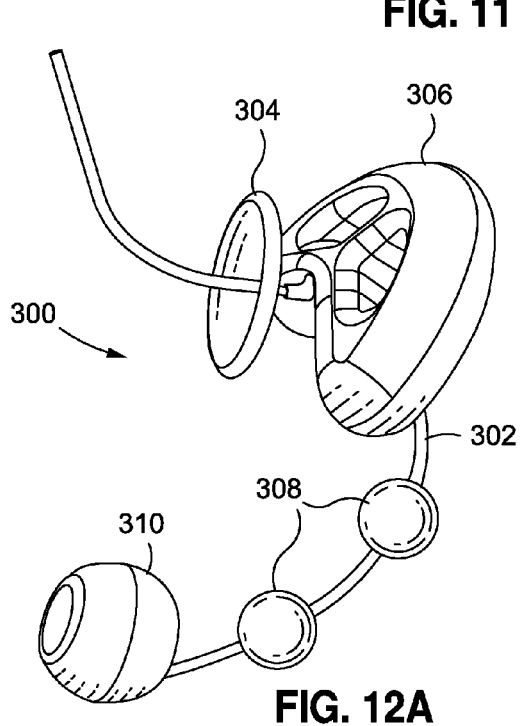
Figure 12B:
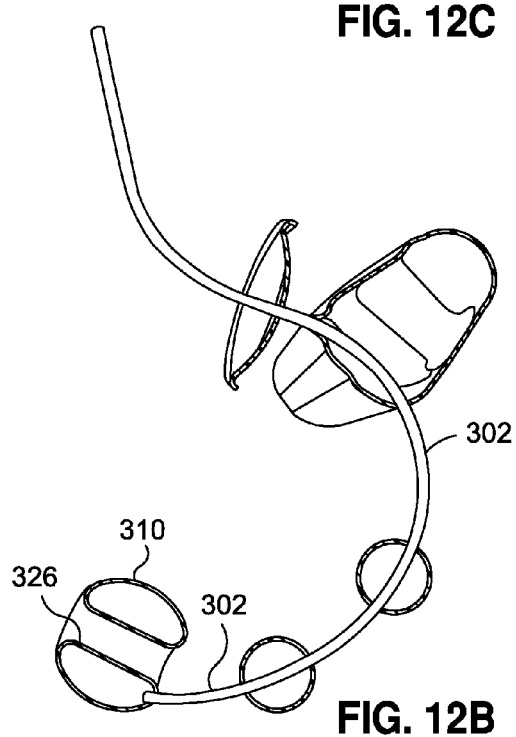

With reference again to FIG. 11, and also to FIGS. 12A-12C, the detention tray 304 is a pliable, shallow conical or bowl-shaped structure with a concave proximal side toward the esophagus. The flexible tether 302 loosely holds the detention tray 304 in place at the proximal end thereof so as to be positioned just below the junction of the esophagus and stomach. That is, the tray 304 is positioned on the tether 302 relative to the pyloric balloon 310 so as to be located adjacent the cardia. The detention tray 304 is preferably not inflatable. The tether 302 projects both distally towards its distal termination at the pyloric balloon 310 and proximally from the tray 304. The proximal end of the tether 304 extends into the lower portion of the esophagus and preferably features a fill valve 312 at its proximal terminus. As the stomach and esophagus undergo normal peristaltic actions, it is expected that the entire device 300 will migrate around to some degree, but most of the time the device is anticipated to return to its normal position as shown, with the tray loosely "sealed" in place against the cardia adjacent the gastro-esophageal junction.

The fill valve 312 at the proximal terminus of the tether 302 allows saline to be added though a detachable fill tube (not shown) inserted down the esophagus, and includes a self-closing slit to hold the saline inside the device 300. Details of an exemplary fill valve 312 will be provided below with reference to FIGS. 16A-16C. The length of the tether 302 runs through the tray 304 and though the hollow balloons 306 and 308 to terminate at the pyloric balloon 310. The distal end of the tether 302 is attached, open-ended inside the annular- or donut-shaped pyloric balloon 310 for filling it with saline. Small side holes (not shown) through the side wall of the tether 302 within the proximal positioning balloon 306 and the intermediate balloons 308 provide for their filling also. The entire series of balloons 306, 308, 310 can therefore be filled after placement within the stomach via the proximal fill valve 312. The proximal end of the tether 302 extending into the esophagus is also intended to help maintain the centered position of the detention tray 304 against the cardia, pressed upwards from the pylorus. During stomach movement the proximal end of the tether 302 may in fact travel downward, loosening the tray intermittently, but the tether shall be of sufficient length to prevent its migration completely out of the esophagus at any time. In one embodiment, the total length of the device 300 from the fill valve 312 to the pyloric balloon 310 is between about 35-40 cm when the tether 302 is measured in a straight line.

Now with particular reference to FIGS. 12A-12C, characteristics of the exemplary balloons 306, 308, 310 will be described. First of all, the intermediate balloons 308 are desirably spherical and identical, but they may also be provided with exterior features (e.g. bumps) such as described below, and they may be dissimilar. The twin spherical intermediate balloons 308 are intended to cushion the tether 302 from directly/sharply touching the greater curvature of the stomach.

The largest balloon, the proximal positioning balloon 306, features an arcuate, generally semi-circular outer section 320 connected at either end to radial spoke sections 322 that meet in the middle along an axis of the structure through which the tether 302 passes. A shorter radial spoke section 324 extends between the outer section 320 and the convergence of the larger spoke sections 322 in the middle of the balloon 320, and generally extends along a plane that bisects the balloon into two symmetric halves. Two apertures 325 formed between the outer section 320 and the spoke sections 322, 324 permit passage of food therethrough such that the positioning balloon 306 does not present a solid barrier to churning movement of food within the stomach. As seen best in FIG. 11, the positioning balloon 306 as viewed from the side has a gradual taper such that its axial thickness, or height, is greater toward the middle of the balloon where the tether 302 passes than at the outer section 320.

Finally, the pyloric balloon 310 has a generally spherical outer shape with a lumen 326 extending axially through the middle to create a donut shape. The lumen 326 through the center of the pyloric balloon permits normal egress of food from the stomach into the duodenum. The inflated pyloric balloon 310 cushions against the pylorus without making a tight seal, but intermittently "sealing" nonetheless. This tends to delay gastric emptying. As seen best in FIG. 12B, the tether 302 terminates within one side of the axi-symmetric balloon 310 and a cavity formed therein extends around 360° so the balloon may be evenly filled via the tether.

Figure 13:
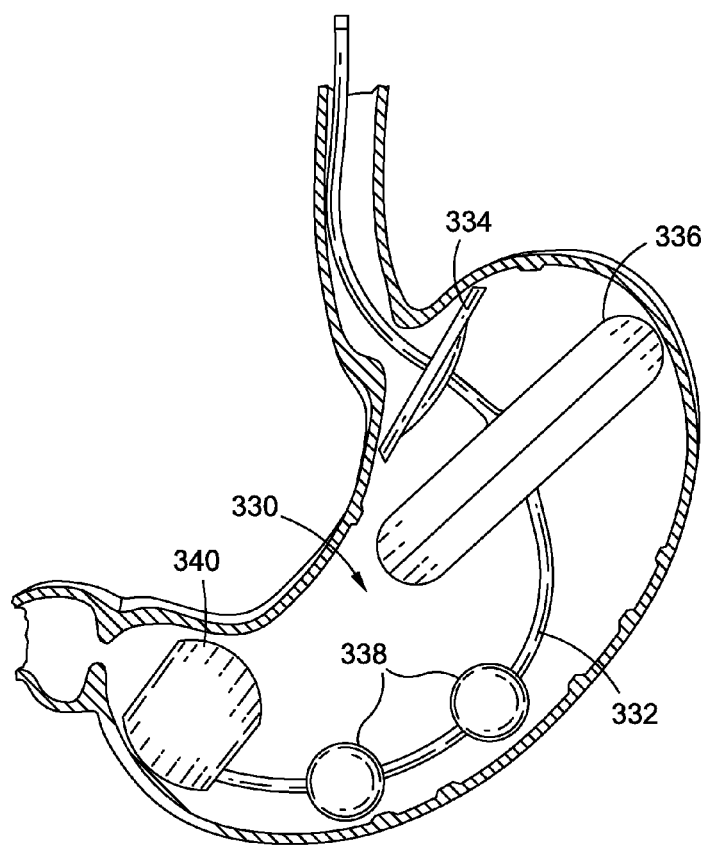
FIG. 13 is a variation of the intragastric device of FIG. 11 having a detention tray below the esophagus, and with an enlarged positioning balloon.
Figure 14A:
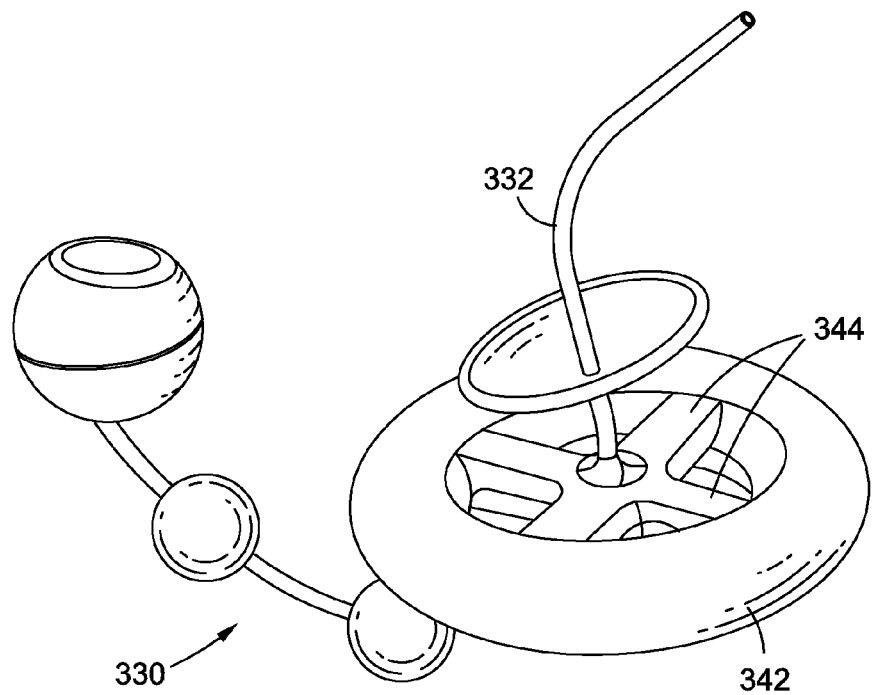
FIGS. 14A-14B are isolated perspective and longitudinal sectional views of the device of FIG. 13.
Figure 14B:
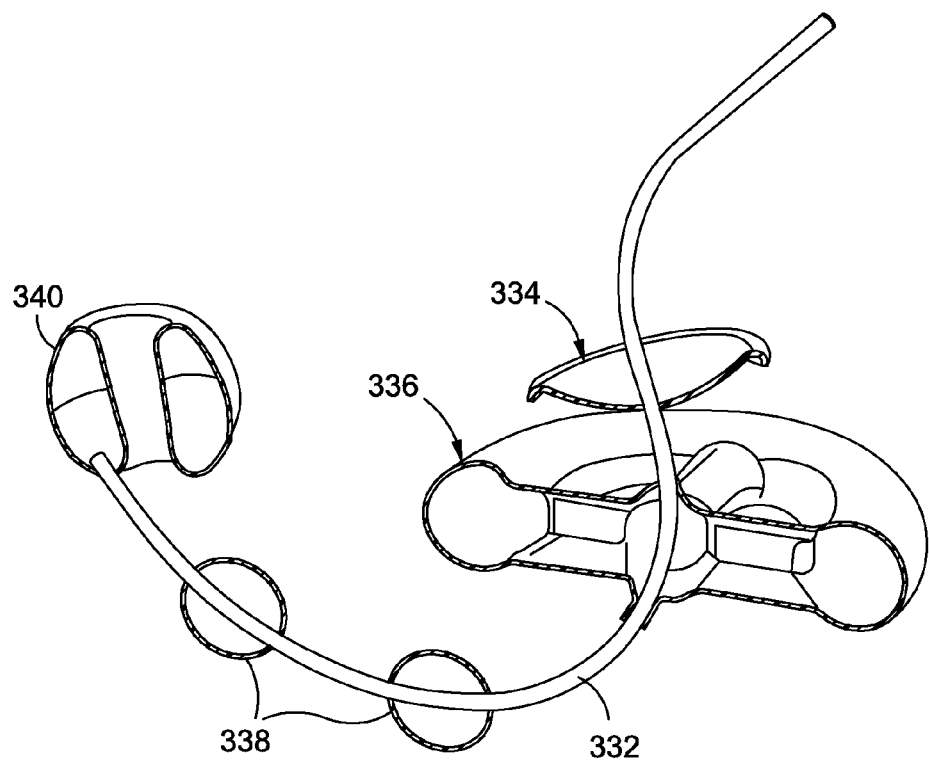

FIG. 13 is a variation of an intragastric device 330 similar to that shown in FIG. 11. The device 330 includes an elongated curved tether 332 that positions a detention tray 334 below the esophagus, and includes an enlarged positioning balloon 336, a pair of intermediate balloons 338, and a pyloric balloon 340. FIGS. 14A-14B show details of the device 330 of FIG. 13. In particular, the enlarged positioning balloon 336 features a complete outer circular section 342 having a pair of diametric perpendicular spokes 344 defining food passages therebetween and extending across a middle portion through which the tether 332 passes. The complete circular section 342 of the positioning balloon 336 may provide improved "anchoring" of the device 330 within the stomach. In other respects the intragastric device 330 is the same as the above-described intragastric device 300.

Figure 15:
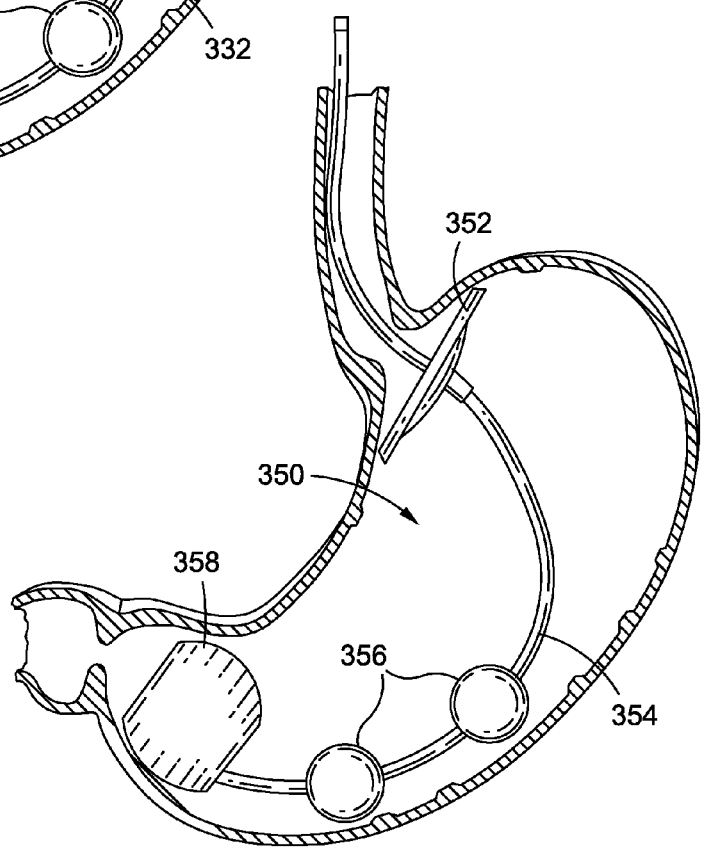
FIG. 15 is still further variation of the intragastric device of FIG. 11 with a detention tray below the esophagus, without a positioning balloon.

FIG. 15 is still further variation of an intragastric device 350 like that of FIG. 11, with a detention tray 352 below the esophagus on a tether 354, but without a proximal positioning balloon. The device 350 still has a pair of intermediate balloons 356 and a distal pyloric balloon 358.

Figure 16A:
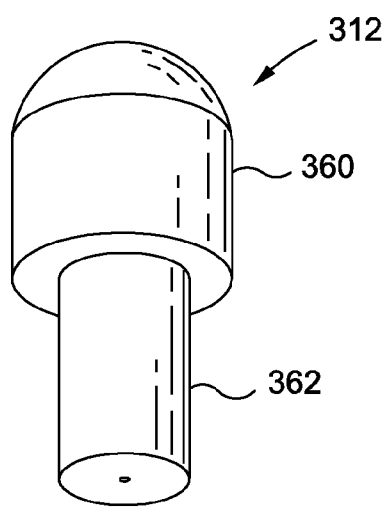
FIGS. 16A-16C are perspective and sectional views of an exemplary fill valve and tube for use with the devices of FIGS. 11, 13 and 15.
Figure 16B:
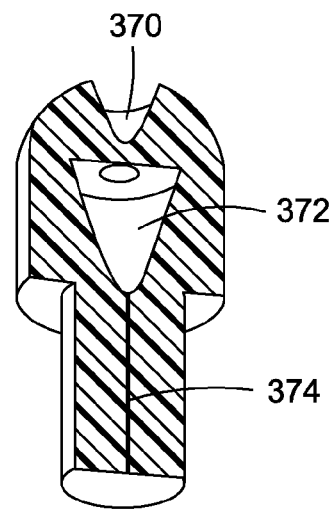
Figure 16C:
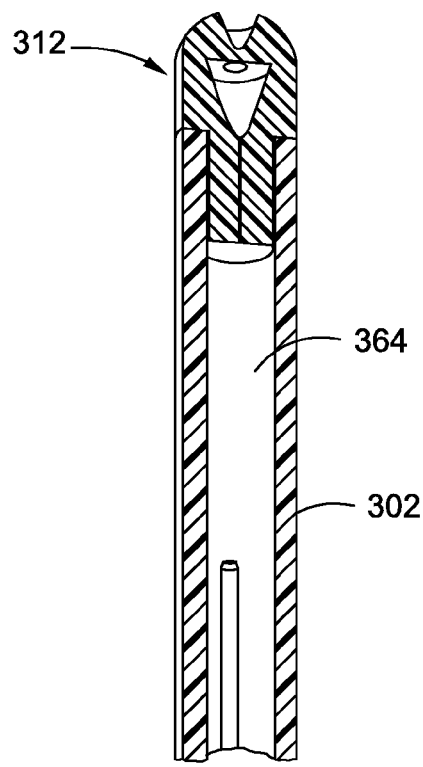

An exemplary fill valve 312 for use with the device 300 of FIG. 11 (and also the devices of FIGS. 13 and 15) is shown in FIGS. 16A-16C. The valve 312 includes an enlarged proximal end 360 which steps down in diameter to a distal insert section 362 that fits tightly within a lumen 364 of the hollow tether 302. A generally inwardly-conical lead-in mouth 370 opens into a retention chamber 372 within the proximal end 360. At the bottom of the retention chamber 372, a slit passage 374 extends through to the distal end of the insert section 362. A fill tube (not shown) has a barbed nipple or other feature that may be forced through the lead-in mouth 370 and captured within the retention chamber 372. Saline under pressure can then be forced through the slit passage 374 and into the lumen 364 of the tether 302. After removal of the fill tube, the slit passage 374 closes up, thus sealing the saline within the device 300 and its daisy-chained balloons.

Figure 17A:
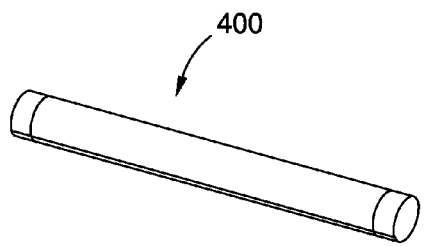
FIGS. 17A-17B illustrate a still further intragastric implant in a contracted, delivery configuration.
Figure 17B:
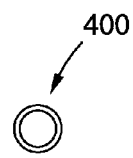
Figure 18A:
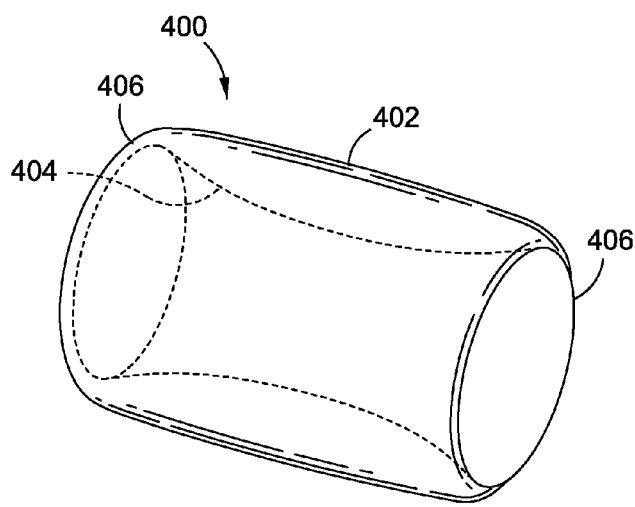
FIGS. 18A-18B illustrate the intragastric implant of FIGS. 17A-17B in an expanded, deployed configuration.
Figure 18B:
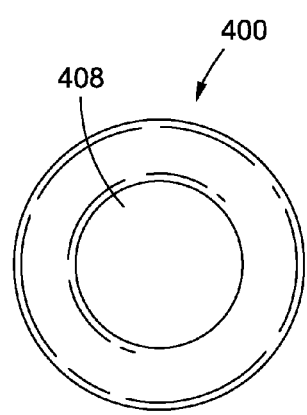

FIGS. 17A-17B illustrate a still further flow-through intragastric implant 400 in a contracted, delivery configuration, while FIGS. 18A-18B illustrate the implant 400 in an expanded, deployed configuration. The implant 400 is in the shape of an inflated tube, with an outer tubular wall 402 joined to an inner tubular wall 404 at circular ends 406. A flow-through lumen 408 extends from end to end. The implant 400 may be delivered in a relatively small tube as seen in FIGS. 17A-17B and then inflated within the stomach to the larger tubular shape of FIGS. 18A-18B. A fill valve (not shown may be provided in the outer wall 402 or at one of the ends 406. The inflated shape in FIG. 18A is relatively short axially and wide in diameter so that it may rotate within the stomach. In a preferred embodiment, the axial dimension is between about 5-10 cm, while the outer diameter is between about 4-8 cm, with the low bound of each range coinciding with the low bound of the other range, and vice versa. Uneven exterior surface features such as described below may be added to further provide stimulation. Additionally, the volume of the implant 400 may occupy approximately the same volume (400 ml) as the aforementioned Orbera® System, which is proven sufficient to facilitate weight loss While not shown, the outer surface of the intragastric devices disclosed herein may further include additional uneven surface features such as small rounded bumps or protrusions, quill-like extensions, dimples or recesses, and the like. These features, upon contact with the inner stomach wall of the patient may further trigger hormone release or otherwise aid the patient in feeling full. Such features may be particularly effective for those embodiments which stimulate the cardia. The examples in FIGS. 19-21 may be applied to any of the various devices and surfaces disclosed herein.

Figure 19:
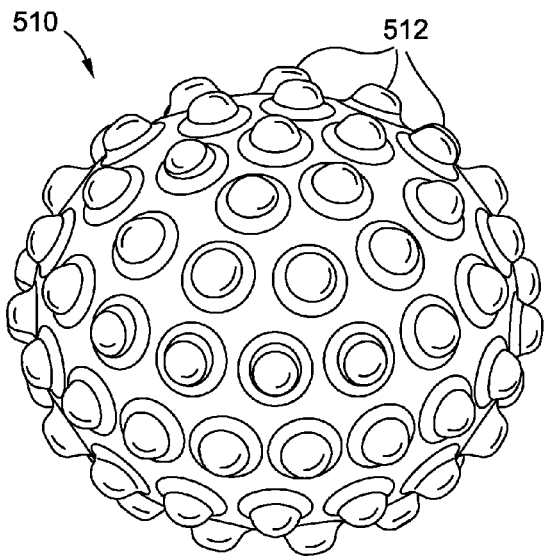
FIGS. 19-21 illustrate intragastric devices that provide additional stomach cavity stimulation.

For instance, FIG. 19 illustrates a spherical intragastric device 510 having numerous external protrusions or bumps 512 projecting outward therefrom. These bumps 512 separately contact the inner walls of the stomach, potentially increasing the stimulation to the surrounding satiety-sensing nerves. As shown, a plurality of bumps 512 may be equally spaced apart on the outer surface and interspersed with flat portions. In one embodiment, the bumps 512 may be of equal heights and diameters, or they may be configured to have different heights and/or diameters. For example, having bumps 512 with different heights and/or diameters may be advantageous for preventing the stomach from adjusting to the bumps. The bumps 512 separately contact the inner walls of the stomach, potentially increasing the stimulation to the surrounding satiety-sensing nerves.

Figure 20:
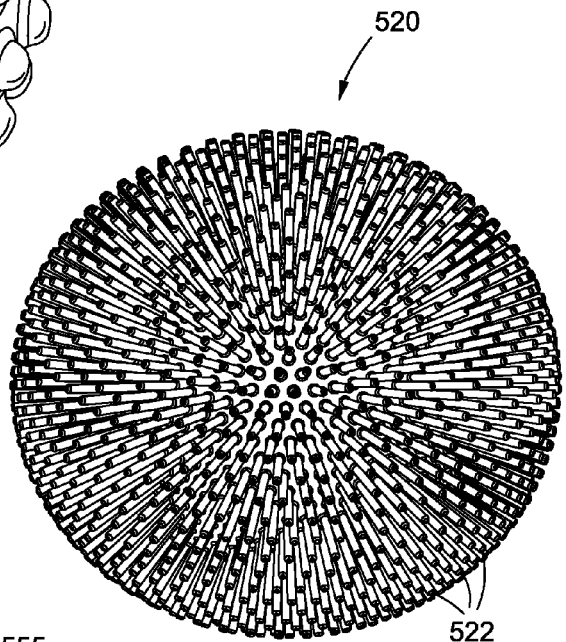

Another example of exterior stimulation features is seen in FIG. 20, where an intragastric device 520 formed as a sphere features a multitude of small flagella or quill-like extensions 522 extending outward therefrom. As shown, a plurality of extensions 522 may be equally spaced apart. In one embodiment, the extensions 522 may be of equal heights and diameters, or they may be configured to have different heights and/or diameters. In one embodiment, the extensions 522 may be extremely flexible and may bend when a pressure is exerted on them from the inner stomach wall of the patient. Alternatively, the extensions 522 may be stiffer and might not bend as much when a pressure is exerted on them from the inner stomach wall of the patient. In another embodiment, some of the extensions 522 may have a first flexibility while some of the extensions may have a second flexibility.

Figure 21:
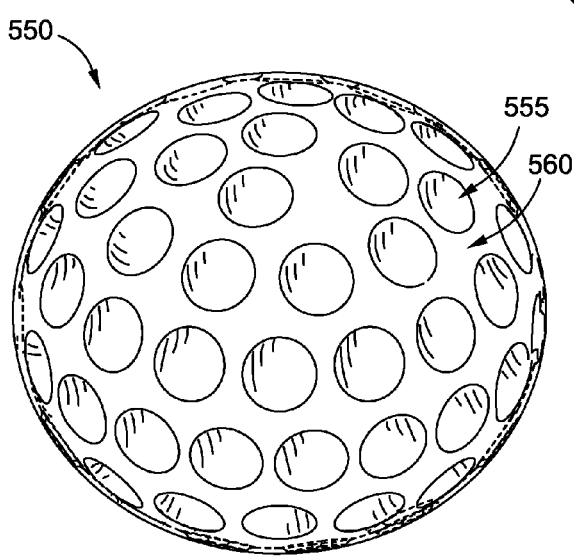

FIG. 21 illustrates another example of uneven surface features on an intragastric device 550. As shown, the intragastric device 550 is a substantially spherical object with recesses or dimples 555 extending inward from the surface of the intragastric device 550. In one embodiment, the intragastric device 550 may be considered to have a surface comprised of recesses 555 and flat portions 560. As shown, a plurality of recesses 555 may be equally spaced apart on the outer surface. As shown, recesses 555 do not contact each other, and may be of equal heights and diameters. In addition to being depressed, the recesses 555 may employ a thinner wall. For example, if the flat portions 560 have a wall thickness of 20 millimeters, the recesses 555 may have a wall thickness of 10 millimeters. With a thinner wall, the recesses 555 may be more susceptible to larger strains. The intragastric device 550 is effectively triggered in the patient's stomach by stomach contractions. These stomach contractions increase the pressure in the intragastric device 550. If one recess 555 is not in contact with the stomach wall, it will deform outward until it comes into contact with the stomach wall.

It should be noted that the embodiments shown in FIGS. 19-21 rotate freely within the stomach, and that the bumps 512, quill-like extensions 522, or recesses 555 may be provided in a non-uniform distribution so as to take advantage of the benefits of the rotational variation described above. That is, a regular array of such exterior features may stimulate the stomach wall more than a smooth surface, but also providing a non-uniform distribution will create different sensations on a constantly changing basis.

It should also be stated that any of the embodiments described herein may utilize materials that improve the efficacy of the device. For example, a number of elastomeric materials may be used including, but not limited to, rubbers, fluorosilicones, fluoroelastomers, thermoplastic elastomers, or any combinations thereof. The materials are desirably selected so as to increase the durability of the device and facilitate implantation of at least six months, and preferably more than 1 year.

Material selection may also improve the safety of the device. Some of the materials suggested herein, for example, may allow for a thinner wall thickness and have a lower coefficient of friction than the current device which may aid in the natural passage of the balloon through the GI tract should the device spontaneously deflate.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems. Applicants propose implanting the devices as described herein into a clinical survey group of obese patients in order to monitor weight loss.

The clinical studies will utilize the devices described above in conjunction with the following parameters.

Materials:
 a. Silicone materials used include 3206 silicone for any shells, inflatable structures, or otherwise flexible hollow structures. Any fill valves will be made from 4850 silicone with 6% $BaSo_4$. Tubular structures or other flexible conduits will be made from silicone rubber as defined by the Food and Drug Administration (FDA) in the Code of Federal Regulations (CFR) Title 21 Section 177.2600.

Purposes:
 a. the devices are for human implant,
 b. the devices are intended to occupy gastric space while also applying intermittent pressure to various and continually changing areas of the stomach;
 c. the devices are intended to stimulate feelings of satiety, thereby functioning as a treatment for obesity.

General Implant Procedures:
 a. The device is intended to be implanted transorally via endoscope into the corpus of the stomach.
 b. Implantation of the medical devices will occur via endoscopy.
 c. Nasal/Respiratory administration of oxygen and isoflurane to be used during surgical procedures to maintain anesthesia as necessary.

One exemplary implant procedure is listed below.
 a. Perform preliminary endoscopy on the patient to examine the GI tract and determine if there are any anatomical anomalies which may affect the procedure and/or outcome of the study.
 b. Insert and introducer into the over-tube.
 c. Insert a gastroscope through the introducer inlet until the flexible portion of the gastroscope is fully exited the distal end of the introducer.
 d. Leading under endoscopic vision, gently navigate the gastroscope, followed by the introducer/over-tube, into the stomach.
 e. Remove gastroscope and introducer while keeping the over-tube in place.
 f. OPTIONAL: Place the insufflation cap on the over-tubes inlet, insert the gastroscope, and navigate back to the stomach cavity.
 g. OPTIONAL: Insufflate the stomach with air/inert gas to provide greater endoscopic visual working volume.
 h. Collapse the gastric implant and insert the lubricated implant into the over-tube, with inflation catheter following if required.
 i. Under endoscopic vision, push the gastric implant down the over-tube with gastroscope until visual confirmation of deployment of the device into the stomach can be determined.
 j. Remove the guide-wire from the inflation catheter is used.
 k. If inflated: Inflate the implant using a standard BioEnterics Intragastric Balloon System ("BIB System") Fill kit.
 l. Using 50-60 cc increments, inflate the volume to the desired fill volume.
 m. Remove the inflation catheter via over-tube.
 n. Inspect the gastric implant under endoscopic vision for valve leakage, and any other potential anomalies. Record all observations.
 o. Remove the gastroscope from over-tube.
 p. Remove the over-tube from the patient.
 End Point Criteria:
 Weight Loss
 Comprehensive Metabolic Panel (CMP)
 HbA1C
 Lipid Panel
 Tissue Samples/Response Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention(especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using "consisting of"or "consisting essentially of"language. When used in the claims, whether as filed or added per amendment, the transition term "consisting of"excludes any element, step, or ingredient not specified in the claims. The transition term "consisting essentially of"limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A passive intragastric obesity treatment implant, comprising:
    an inflatable body having a length sufficient to extend between the esophageal sphincter at a superior end of the body and the pyloric sphincter at an inferior end of the body upon implant in the stomach, and a width sufficient to contact the interior stomach walls upon contraction thereof, the body being rounded and slightly tapered so as to generally conform to the volume of an adult stomach cavity, the body including a series of chambers fluidly connected so as to be capable of simultaneous inflation and deflation, wherein two chambers at the superior end are separated from each other by an annular recess that is positioned to open to the esophageal sphincter, and wherein apertures in the annular recess open to a central flow channel that extends from the annular recess to the inferior end of the body, wherein the central flow channel extends through at least two chambers between the annular recess and the inferior end of the body,
    the implant being formed of a material which permits it to be compressed into a substantially linear delivery configuration and that will resist degradation over a period of at least six months within the stomach.

2. The implant of claim 1, wherein the central flow channel has a star-shaped cross-section.

3. The implant of claim 1, wherein the chambers gradually decrease in diameter from the superior to the inferior ends of the body.

4. The implant of claim 1, wherein the body includes a rounded superior end that mimics the shape of the surrounding cardia and defines a proximal chamber therein.

5. The implant of claim 1, wherein an outer surface of the inflatable body includes uneven surface features.

6. The implant of claim 5, wherein the uneven surface features include at least one of a rounded bump or protrusion, quill-like extension, flagella, dimple, and recess.

7. The implant of claim 6, wherein the uneven surface features are equally spaced from each other along the outer surface of the inflatable body.

8. The implant of claim 6, wherein the uneven surface features have different heights.

9. The implant of claim 6, wherein the uneven surface features flex in response to a pressure being exerted on them from the inner stomach wall of the patient.

10. The implant of claim 5, wherein the uneven surface features are constructed to contact the inner stomach to trigger hormone release.

11. The implant of claim 5, wherein the uneven surface features are constructed to contact the inner stomach to stimulate the cardia.

12. A passive intragastric obesity treatment implant, comprising:
    an inflatable body having a length sufficient to extend between the esophageal sphincter at a superior end of the body and the pyloric sphincter at an inferior end of the body upon implant in the stomach, and a width sufficient to contact the interior stomach walls upon contraction thereof, the body being rounded and slightly tapered so as to generally conform to the volume of an adult stomach cavity, the body including a series of chambers fluidly connected so as to be capable of simultaneous inflation and deflation, wherein two chambers at the superior end are separated by an annular recess that is positioned to open to the esophageal sphincter, and wherein apertures in the annular recess open to a central flow channel that extends from the annular recess to the inferior end of the body, and some of the chambers surround the central flow channel, the implant being formed of a material which permits it to be compressed into a substantially linear delivery configuration and that will resist degradation over a period of at least six months within the stomach, wherein a plurality of circumferential grooves extend around the body and between adjacent chambers, and wherein radial passages connect the circumferential grooves to the central flow channel.

13. A passive intragastric obesity treatment implant, comprising:

an inflatable body having a length sufficient to extend between the esophageal sphincter at a superior end of the body and the pyloric sphincter at an inferior end of the body upon implant in the stomach, and a width sufficient to contact the interior stomach walls upon contraction thereof, the body being rounded and slightly tapered so as to generally conform to the volume of an adult stomach cavity, the body including a series of annular chambers in fluid communication with an inner longitudinal channel that extends through the annular chambers for simultaneous inflation and deflation of the annular chambers, wherein the chamber at the superior end is longitudinally spaced from a proximal chamber of the body by an annular recess that is positioned to be open to the esophageal sphincter, and wherein transverse flow channels are formed in the annular recess that extend to the inner longitudinal channel in a direction transverse to the longitudinal channel, wherein the longitudinal channel extends from the annular recess to the inferior end of the body, wherein the longitudinal flow channel extends through at least two chambers between the annular recess and the inferior end of the body, the implant being formed of a material which permits it to be compressed into a substantially linear delivery configuration and that will resist degradation over a period of at least six months within the stomach.

14. The implant of claim 13, wherein the annular chambers gradually decrease in outer diameter from the superior to the inferior ends of the body.

15. The implant of claim 13, wherein the body includes a rounded superior end that mimics the shape of the inner wall of the surrounding cardia and defines a proximal chamber therein.

16. The implant of claim 13, wherein an outer surface of the inflatable body includes uneven surface features.

17. The implant of claim 16, wherein the uneven surface features include at least one of a rounded bump or protrusion, quill-like extension, flagella, dimple, and recess.

18. The implant of claim 17, wherein the uneven surface features are equally spaced from each other along the outer surface of the inflatable body.

19. The implant of claim 17, wherein the uneven surface features have different heights.

20. The implant of claim 17, wherein the uneven surface features flex in response to a pressure being exerted on them from the inner stomach wall of the patient.

21. The implant of claim 16, wherein the uneven surface features are constructed to contact the inner stomach to trigger hormone release.

22. The implant of claim 16, wherein the uneven surface features are constructed to contact the inner stomach to stimulate the cardia.

23. A passive intragastric obesity treatment implant, comprising:

an inflatable body having a length sufficient to extend between the esophageal sphincter at a superior end of the body and the pyloric sphincter at an inferior end of the body upon implant in the stomach, and a width sufficient to contact the interior stomach walls upon contraction thereof, the body being rounded and slightly tapered so as to generally conform to the volume of an adult stomach cavity, the body including a series of annular chambers in fluid communication with an inner longitudinal channel that extends through the annular chambers for simultaneous inflation and deflation of the annular chambers, wherein the chamber at the superior end is longitudinally spaced from a proximal chamber of the body by an annular recess that is positioned to open to the esophageal sphincter, and wherein transverse flow channels are formed in the annular recess that extend to the inner longitudinal channel in a direction transverse to the longitudinal channel, wherein the longitudinal channel extends from the annular recess to the inferior end of the body, the implant being formed of a material which permits it to be compressed into a substantially linear delivery configuration and that will resist degradation over a period of at least six months within the stomach, wherein the inner longitudinal channel has a star-shaped cross-section.

24. A passive intragastric obesity treatment implant, comprising:

an inflatable body having a length sufficient to extend between the esophageal sphincter at a superior end of the body and the pyloric sphincter at an inferior end of the body upon implant in the stomach, and a width sufficient to contact the interior stomach walls upon contraction thereof, the body being rounded and slightly tapered so as to generally conform to the volume of an adult stomach cavity, the body including a series of annular chambers in fluid communication with an inner longitudinal channel that extends through the annular chambers for simultaneous inflation and deflation of the annular chambers, wherein the chamber at the superior end is longitudinally spaced from a proximal chamber of the body by an annular recess that is positioned to open to the esophageal sphincter, and wherein transverse flow channels are formed in the annular recess that extend to the inner longitudinal channel in a direction transverse to the longitudinal channel, wherein the longitudinal channel extends from the annular recess to the inferior end of the body, the implant being formed of a material which permits it to be compressed into a substantially linear delivery configuration and that will resist degradation over a period of at least six months within the stomach, wherein a plurality of circumferential grooves extend around the body and between adjacent annular chambers, and wherein transverse passages connect the circumferential grooves to the inner longitudinal channel.

\* \* \* \* \*